US012796948B2

(12) United States Patent
Ochi et al.

(10) Patent No.: US 12,796,948 B2
(45) Date of Patent: Nov. 17, 2026

(54) SENSOR UNIT AND MEDICAL IMAGE CAPTURING APPARATUS

(71) Applicant: FUJIFILM Corporation, Tokyo (JP)

(72) Inventors: Hisaaki Ochi, Tokyo (JP); Yukio Kaneko, Tokyo (JP); Toru Shirai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/095,752

(22) Filed: Mar. 31, 2025

(65) Prior Publication Data

US 2025/0302322 A1 Oct. 2, 2025

(30) Foreign Application Priority Data

Apr. 1, 2024 (JP) ................................ 2024-059241

(51) Int. Cl.
*A61B 5/024* (2006.01)
*A61B 5/00* (2006.01)
(Continued)

(52) U.S. Cl.
CPC .......... *A61B 5/02427* (2013.01); *A61B 5/055* (2013.01); *A61B 5/6892* (2013.01); *A61B 5/704* (2013.01); *A61B 2034/2061* (2016.02)

(58) Field of Classification Search
CPC ...... G16H 50/20; A61B 5/0205; A61B 5/024; A61B 5/02427; A61B 5/704;
(Continued)

(56) References Cited

U.S. PATENT DOCUMENTS

2003/0095263 A1 5/2003 Varshneya et al.
2008/0085074 A1 4/2008 Wakahara et al.
(Continued)

FOREIGN PATENT DOCUMENTS

JP 2007-061306 A 3/2007
JP 2014-534848 A 12/2014
(Continued)

OTHER PUBLICATIONS

Dziuda, L. et al.; "Fiber Bragg Grating Strain Sensor Incorporated to Monitor Patient Vital Signs During MRI"; IEEE Sensors Journal; Dec. 2013; pp. 4986-4991; vol. 13, No. 12; IEEE; XP011529234; ISSN: 1530-437X; URL: https://ieeexplore.ieee.org/document/6585757.

(Continued)

*Primary Examiner* — Gerald Johnson
(74) *Attorney, Agent, or Firm* — Studebaker Brackett PLLC

(57) ABSTRACT

Provided are a sensor unit and a medical image capturing apparatus in which movement of the sensor unit caused by movement of a subject is suppressed. The sensor unit is attached to a surface on which a subject is placed and detects a heartbeat of the subject, and includes an FBG sensor that is provided with one or more sensor elements for detecting the heartbeat of the subject, a fixing member that fixes a side of the FBG sensor opposite to a side facing the subject and that has a surface on which the FBG sensor is fixed, the surface having a predetermined stiffness, and a cover that covers the side of the FBG sensor facing the subject and that has a structure in which a cover hole is formed at a position corresponding to the sensor element on a surface of the side facing the subject.

18 Claims, 23 Drawing Sheets

(51) Int. Cl.
*A61B 5/055* (2006.01)
*A61B 34/20* (2016.01)

(58) Field of Classification Search
CPC ...... A61B 2090/3954; A61B 2576/023; A61B 5/6869; A61B 5/02158; A61B 5/6838
See application file for complete search history.

(56) References Cited

U.S. PATENT DOCUMENTS

| | | | |
|---|---|---|---|
| 2008/0221488 A1 | 9/2008 | Kurono et al. | |
| 2009/0185772 A1 | 7/2009 | Xia et al. | |
| 2025/0127458 A1* | 4/2025 | Popescu ............... | A61B 5/1126 |

FOREIGN PATENT DOCUMENTS

| | | |
|---|---|---|
| JP | 2020-138022 A | 9/2020 |
| WO | 2013/180085 A1 | 12/2013 |

OTHER PUBLICATIONS

Extended European Search Report issued in EP 25 16 7537.7-1113 by the European Patent Office on May 14, 2025, which is related to U.S. Appl. No. 19/095,752.

Communication pursuant to Article 94(3) EPC issued in EP 25 167 537.7-1113 by the European Patent Office on May 26, 2026.

Wang, Liqing, et al.; "A wearable FBG pulse-wave sensor based on multilayers compound fabrics structure"; Proceedings of SPIE; Oct. 23, 2018; pp. 1-8; vol. 10821; SPIE, Bellingham, WA. ISSN: 0277-786X. DOI: 10.1117/12.2322610. ISBN: 9781510620995.

* cited by examiner

EXAMPLE OF DRIFT IN MEASUREMENT WAVEFORM OF NON-FIXED FBG OPTICAL FIBER OR THE LIKE

SENSOR UNIT AND MEDICAL IMAGE CAPTURING APPARATUS

CROSS-REFERENCE TO RELATED APPLICATION

The present application claims priority under 35 U.S.C § 119 (a) to Japanese Patent Application No. 2024-059241 filed on Apr. 1, 2024, which is hereby expressly incorporated by reference, in its entirety, into the present application.

BACKGROUND OF THE INVENTION

1. Field of the Invention

The present disclosure relates to a sensor unit and a medical image capturing apparatus.

2. Description of the Related Art

In a medical image capturing apparatus such as an MRI apparatus, in a case of imaging a heart, in general, a heartbeat is monitored, and an MR signal is measured while synchronizing the heartbeat. In addition, in a case of performing the hemodynamic imaging of a part away from the heart, such as the brain and the lower limb, using an MRI apparatus or the like, the heartbeat may also be monitored. In addition, MRI is an abbreviation for Magnetic Resonance Imaging.

As a method of monitoring a heartbeat, there is a method of measuring an electrocardiographic waveform by installing an electrode in which a conductive gel is attached to the skin near the heart of a subject. As another method of monitoring a heartbeat, there is a method of measuring a pulse waveform in which a change in blood flow that changes in accordance with the heartbeat is captured as a change in infrared light in a case where the fingertip of the subject is irradiated with the infrared light. In any of the above-described methods, a peak of the electrocardiographic waveform and a peak of the pulse waveform in a ventricular systole in a case where the movement of the heart of the subject is the largest are captured, and are used as a time trigger in a case of measuring an MR signal.

WO2013/180085A describes an optical fiber sensor system comprising an FBG sensor, which separates and detects a signal associated with a pulse wave at a measurement site for each measurement site. The FBG sensor is an abbreviation for a fiber Bragg grating sensor.

In the optical fiber sensor system described in WO2013/180085A, the FBG sensor is attached to the skin surface of a measurement site where it is easy to detect the expansion and contraction of the artery of the chest or the like of the subject, the FBG sensor detects a slight displacement of the skin surface associated with the expansion and contraction of the artery to detect the pulse wave of the subject.

In the optical fiber sensor system described in WO2013/180085A, an optical fiber in which a plurality of FBG sensors are arranged in series is used in a case where pulse waves at a plurality of locations are detected using the FBG sensors. The plurality of FBG sensors have different Bragg wavelengths from each other. In the optical fiber sensor system, light incident on the optical fiber is light in a band including the Bragg wavelength of the FBG sensor, and the optical signal of each of the FBG sensors is separated and detected.

JP2014-534848A describes a sensing fiber including one or a plurality of optical fiber Bragg gratings. FIG. 2 of JP2014-534848A shows the sensing fiber integrated into the vest. In JP2014-534848A, a magnetic resonance imaging system is exemplified as an imaging system that images the inside of the subject.

JP2007-061306A discloses an optical fiber type flat body sensor used in a method of detecting breathing, pulsation, and the like with high accuracy. In the optical fiber type flat body sensor described in JP2007-061306A, a plurality of filters that reflect specific wavelengths, such as an optical fiber diffraction grating, are incorporated in the middle of the optical fiber. In addition, JP2007-061306A describes, as an example of installation of the optical fiber type flat body sensor, an aspect in which the optical fiber type flat body sensor is installed between a pad and a mat on a bed.

JP2020-138022A describes a system that detects a pulse wave using an FBG sensor and calculates a heart rate. JP2020-138022A describes that a pulse wave is measured using an FBG sensor attached to a surface of the chest, and data is acquired using an FBG sensor having a plurality of point sensor portions. In addition, JP2020-138022A describes that the FBG sensor is fixed to the abdomen of the pregnant woman to perform measurement, and the fetal signal is measured from the measured waveform.

In addition, as a method of monitoring a heartbeat other than the electrocardiographic measurement and the pulse wave measurement, a method of measuring a change in a shape of a heart using electromagnetic waves and capturing a peak of a ventricular systole has been proposed. In a method of monitoring a heartbeat using electromagnetic waves, the heartbeat monitoring antenna is installed in a part of a heart imaging receive coil installed in the vicinity of the heart in a case of imaging the heart of the subject, and a change in impedance of the antenna accompanying a change in shape of the heart, in a case where an RF pulse is applied, is measured.

SUMMARY OF THE INVENTION

However, in the electrocardiographic waveform measurement, in a case of installing electrodes, an operator or the like installs the electrodes at an appropriate position in a state where the subject is undressed. In this case, both the subject and the operator may be mentally and temporally burdened. In addition, in the electrocardiographic waveform measurement, in a case where the subject sweats during imaging and the electrode is detached from the subject, it is difficult to monitor the heartbeat.

The invention described in WO2013/180085A and the invention described in JP2014-534848A have problems of mental burden and time burden on the subject and the operator in the installation of the sensor element on the subject. In addition, the invention described in WO2013/180085A has a problem that it is difficult to monitor the heartbeat due to the detachment of the sensor element installed on the subject.

In the measurement of the pulse waveform of the subject, the measurement is performed at the fingertip away from the heart as compared with the electrocardiographic waveform measurement, so that a peak of the electrocardiographic waveform measurement in the ventricular systole is dull. The measurement of the pulse waveform of the subject is not suitable for high-accuracy monitoring of the heartbeat.

In general, in a posture in which the subject is lying down, the pulse wave fluctuation at sites away from the heart, such as a fingertip, is smaller than the pulse wave fluctuation at sites close to the heart, such as the chest. In this case, there is a concern that the fluctuation of the pulse waveform in the fingertip during the imaging becomes small, and the peak of the pulse waveform cannot be acquired.

The method of monitoring a heartbeat using electromagnetic waves has an advantage that the measurement can be performed while the subject is wearing clothes, and the mental burden and the time burden on both the subject and the imaging person are smaller than those in the electrocardiographic measurement. In addition, the method of monitoring a heartbeat using electromagnetic waves has an advantage that a sensor for monitoring the heartbeat is installed near the heart and a pulse waveform does not become dull to extent that the peak of the pulse waveform cannot be acquired during the imaging, as in a method of measuring the pulse wave of the fingertip.

On the other hand, in the method of monitoring a heartbeat using electromagnetic waves, in a case where a hemodynamics of an imaging site away from the heart, such as a brain and a lower limb, is imaged in synchronization with the heartbeat, it is necessary to install the imaging site at the center of the irradiation coil. In this case, the antenna for monitoring a heartbeat, which is disposed in the vicinity of the heart, may be significantly deviated from the center of the bore, and it may be difficult to apply the method of monitoring a heartbeat using electromagnetic waves.

In addition, the method of monitoring the heartbeat using electromagnetic waves may have a limitation that it is difficult to monitor the heartbeat to which sufficient temporal resolution is applied in a sequence in which the irradiation pulse interval is long. A method of monitoring a heartbeat using an FBG sensor or the like installed other than the body of the subject and the clothing of the subject solves the problems of the method of monitoring a heartbeat using electromagnetic waves described above.

In the method of monitoring a heartbeat using an FBG sensor or the like, in a case where the FBG sensor or the like is not fixed to a rigid object such as a heavy object, the FBG sensor or the like may move in a three-dimensional space due to a movement of a body of the subject, and a drift may occur in the electrocardiographic waveform.

In general, the movement of the body of the subject is larger than the movement of the skin associated with the heartbeat by 10 times or more, and it is difficult to monitor the heartbeat that captures a small change in the waveform during a period in which the electrocardiographic waveform drifts due to the movement of the body of the subject.

In the invention described in JP2014-534848A in which the sensing fiber installed in the vest of the subject is used, the vest also moves due to the movement of the body of the subject, and there is a concern about the occurrence of drift in the electrocardiographic waveform. During a period in which the drift occurs in the electrocardiographic waveform, it is difficult to monitor the heartbeat, and in a case where the subject is imaged while synchronizing with the heartbeat using an MRI apparatus or the like, the imaging period is extended with respect to a predetermined imaging period.

The measurement waveform output from the FBG sensor measures reflected light from the diffraction grating, and even in a case where the optical fiber connecting the diffraction grating and the interrogator, which is a propagation path of the reflected light, moves, the drift may occur in the electrocardiographic waveform in the same manner as in a case where the body of the subject moves. During a period in which the drift occurs in the electrocardiographic waveform, it is difficult to monitor the heartbeat. That is, it is preferable that the optical fiber connecting the diffraction grating and the interrogator is not subjected to vibration, pressure, or the like.

In a case where the invention described in JP2007-061306A, in which an optical fiber type flat body sensor installed between a pad and a mat placed under the subject is used, is applied to monitoring of a heartbeat in an MRI apparatus or the like, a position of the optical fiber type flat body sensor is moved in a three-dimensional space due to movement of hands and feet of the subject, and thus an unpredictable drift may occur in an electrocardiographic waveform. During a period in which the drift occurs in the electrocardiographic waveform, it is difficult to monitor the heartbeat.

In a case where the invention described in JP2020-138022A, in which the FBG sensor is fixed to the abdomen of the subject to perform measurement, is applied to monitoring of the heartbeat in an MRI apparatus or the like, the unpredictable drift may occur in the electrocardiographic waveform due to the unpredictable movement of the subject. During a period in which the drift occurs in the electrocardiographic waveform, it is difficult to monitor the heartbeat.

The present disclosure has been made in consideration of such circumstances, and an object of the present disclosure is to provide a sensor unit and a medical image capturing apparatus in which movement of the sensor unit caused by movement of a subject is suppressed.

A sensor unit according to a first aspect of the present disclosure is a sensor unit that is attached to a surface on which a subject is placed in a bed on which the subject is placed and that detects a heartbeat of the subject, the sensor unit comprising: a fiber Bragg grating sensor that is provided with one or more sensor elements for detecting the heartbeat of the subject; a fixing member that fixes a side of the fiber Bragg grating sensor opposite to a side facing the subject and that has a surface on which the fiber Bragg grating sensor is fixed, the surface having a predetermined stiffness; and a cover that covers the side of the fiber Bragg grating sensor facing the subject and that has a structure in which a cover hole is formed at a position corresponding to the sensor element on a surface of the side facing the subject.

According to the sensor unit according to the first aspect, the fiber Bragg grating sensor is fixed to the fixing member having the predetermined stiffness, and the cover that covers the side facing the subject is provided. As a result, the movement of the fiber Bragg grating sensor caused by the movement of the subject is suppressed. On the other hand, the sensor element comes into contact with the subject via the cover hole. As a result, the detection of the heartbeat of the subject is preferably achieved.

According to a sensor unit according to a second aspect, in the sensor unit according to the first aspect, the sensor unit further comprises a contact assisting member that is disposed at a position corresponding to the sensor element in the fiber Bragg grating sensor and located on a side of the cover hole, and that has a shape protruding from the cover hole.

According to a sensor unit according to a third aspect, in the sensor unit according to the second aspect, in the contact assisting member, a length of a first surface to be brought into contact with the subject is longer than a length of a second surface to be brought into contact with the sensor element, in a longitudinal direction of the bed on which the sensor unit is installed.

According to a sensor unit according to a fourth aspect, in the sensor unit according to the first to third aspects, the sensor unit further comprises a first elastic member that is installed at a position corresponding to the sensor element in the fiber Bragg grating sensor and located on a side of the fixing member, and that has predetermined elasticity.

According to a sensor unit according to a fifth aspect, in the sensor unit according to the first to fourth aspects, the sensor unit further comprises a second elastic member that is installed on the fixing member, has predetermined elasticity, and has a thickness that comes into contact with the subject.

According to a sensor unit according to a sixth aspect, in the sensor unit according to the first to fifth aspects, the fixing member is installed on the bed and also serves as a table on which the subject is placed.

According to a sensor unit according to a seventh aspect, in the sensor unit according to the first to fifth aspects, the fixing member has a shape that follows a shape of a surface of a table installed on the bed, on which the sensor unit is installed.

According to a sensor unit according to an eighth aspect, in the sensor unit according to the first to seventh aspects, the cover has a shape that covers an entire length of the fiber Bragg grating sensor in a direction in which the fiber Bragg grating sensor extends.

According to a sensor unit according to a ninth aspect, in the sensor unit according to the eighth aspect, the cover has a shape in which the direction in which the fiber Bragg grating sensor extends is a longitudinal direction.

According to a sensor unit according to a tenth aspect, in the sensor unit according to the eighth aspect, the cover has a polygonal or circular planar shape on a surface on which the fiber Bragg grating sensor extends.

According to a sensor unit according to an eleventh aspect, in the sensor unit according to the first to tenth aspects, the fiber Bragg grating sensor includes a first sensor element and a second sensor element that is different from the first sensor element, and the cover has a first cover hole formed at a position corresponding to the first sensor element and a second cover hole formed at a position corresponding to the second sensor element.

According to a sensor unit according to a twelfth aspect, in the sensor unit according to the eleventh aspect, the sensor unit further comprises: a first contact assisting member that is disposed at the position corresponding to the first sensor element in the fiber Bragg grating sensor and that has a shape protruding from the first cover hole; and a second contact assisting member that is disposed at the position corresponding to the second sensor element in the fiber Bragg grating sensor and that has a shape protruding from the second cover hole.

According to a sensor unit according to a thirteenth aspect, in the sensor unit according to the twelfth aspect, the sensor unit further comprises: a first fiber Bragg grating sensor including the first sensor element; and a second fiber Bragg grating sensor including the second sensor element.

A medical image capturing apparatus according to a fourteenth aspect of the present disclosure comprises: a bed on which a subject is placed; a measurement device that measures the subject; a measurement data processing device that generates a medical image of the subject based on a measurement result of the subject; and a sensor unit that is attached to a surface on which the subject is placed in the bed and that detects a heartbeat of the subject, in which the sensor unit includes a fiber Bragg grating sensor that includes one or more sensor elements that detect the heartbeat of the subject, a fixing member that fixes a side of the fiber Bragg grating sensor opposite to a side facing the subject and that has a surface on which the fiber Bragg grating sensor is fixed, the surface having a predetermined stiffness, and a cover that covers the side of the fiber Bragg grating sensor facing the subject and that has a structure in which a cover hole is formed at a position corresponding to the sensor element on a surface of the side facing the subject.

With the medical image capturing apparatus according to the fourteenth aspect of the present disclosure, the same actions and effects as those of the sensor unit according to the first aspect can be obtained. The configuration requirements of the sensor unit according to the second to thirteenth aspects can be applied as configuration requirements of a medical image capturing apparatus according to other aspects.

According to a medical image capturing apparatus according to a fifteenth aspect, in the medical image capturing apparatus according to the fourteenth aspect, the medical image capturing apparatus further comprises one or more processors, in which the one or more processors select one sensor element from among a plurality of sensor elements based on a captured image in which the subject is imaged.

According to a medical image capturing apparatus according to a sixteenth aspect, in the medical image capturing apparatus according to the fourteenth or fifteenth aspect, the fixing member is installed on the bed and also serves as a coil unit installed on a table on which the subject is placed.

According to a medical image capturing apparatus according to a seventeenth aspect, in the medical image capturing apparatus according to the sixteenth aspect, the fiber Bragg grating sensor is embedded in a plate-shaped member on a side opposite to the table in a housing in which a coil provided in the coil unit is housed.

According to the present disclosure, the fiber Bragg grating sensor is fixed to the fixing member having the predetermined stiffness, and the cover that covers the side facing the subject is provided. As a result, the movement of the fiber Bragg grating sensor caused by the movement of the subject is suppressed. On the other hand, the sensor element comes into contact with the subject via the cover hole. As a result, the detection of the heartbeat of the subject is preferably achieved.

DESCRIPTION OF THE PREFERRED EMBODIMENTS

Figure 1:
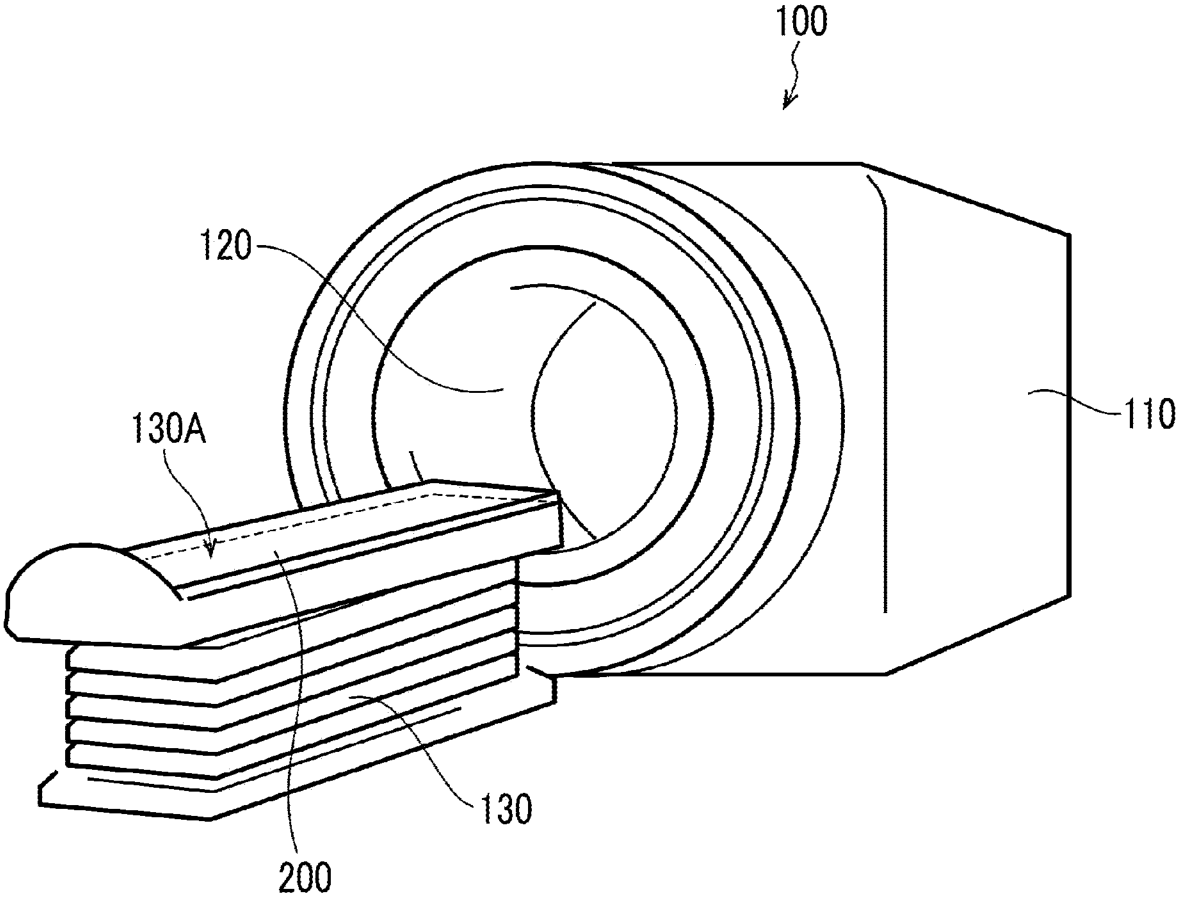
FIG. 1 is a perspective view showing an appearance of an MRI apparatus.

Hereinafter, a preferred embodiment of the present invention will be described in detail with reference to the accompanying drawings. In the following description and the accompanying drawings, the same constituent elements are denoted by the same reference numerals, and the duplicated description thereof is omitted. In addition, in the following embodiment, in a case in which a plurality of constituent elements are described and listed, it can be interpreted that at least one of the plurality of constituent elements is included. Configuration Example of MRI apparatus FIG. 1 is a perspective view showing an appearance of an MRI apparatus. An MRI apparatus 100, which is a magnetic resonance imaging apparatus, comprises a gantry 110, which is an apparatus main body, and a bed 130. The bed 130 comprises a top plate 130A and is disposed on a front side of a bore 120, which is a cylindrical-shaped imaging space provided in the gantry 110. The top plate 130A can be made to enter the bore 120 using a top plate drive mechanism provided in the bed 130, and can be made to exit from the bore 120. The top plate drive mechanism is not shown.

The bed 130 may be configured to be fixed to the gantry 110, or may be a dockable bed which is a mobile bed that can be attached to and detached from the gantry 110. The top plate 130A provided in the bed 130 is configured to be freely attachable to and detachable from a sensor unit 200. The sensor unit 200 is used in a case where the heartbeat of a subject is monitored. The subject is denoted by a reference numeral Exa and is shown in FIG. 2 and the like.

The gantry 110 is an example of a measurement device according to the present disclosure. The MRI apparatus is an example of a medical image capturing apparatus according to the embodiment of the present disclosure.

Figure 2:
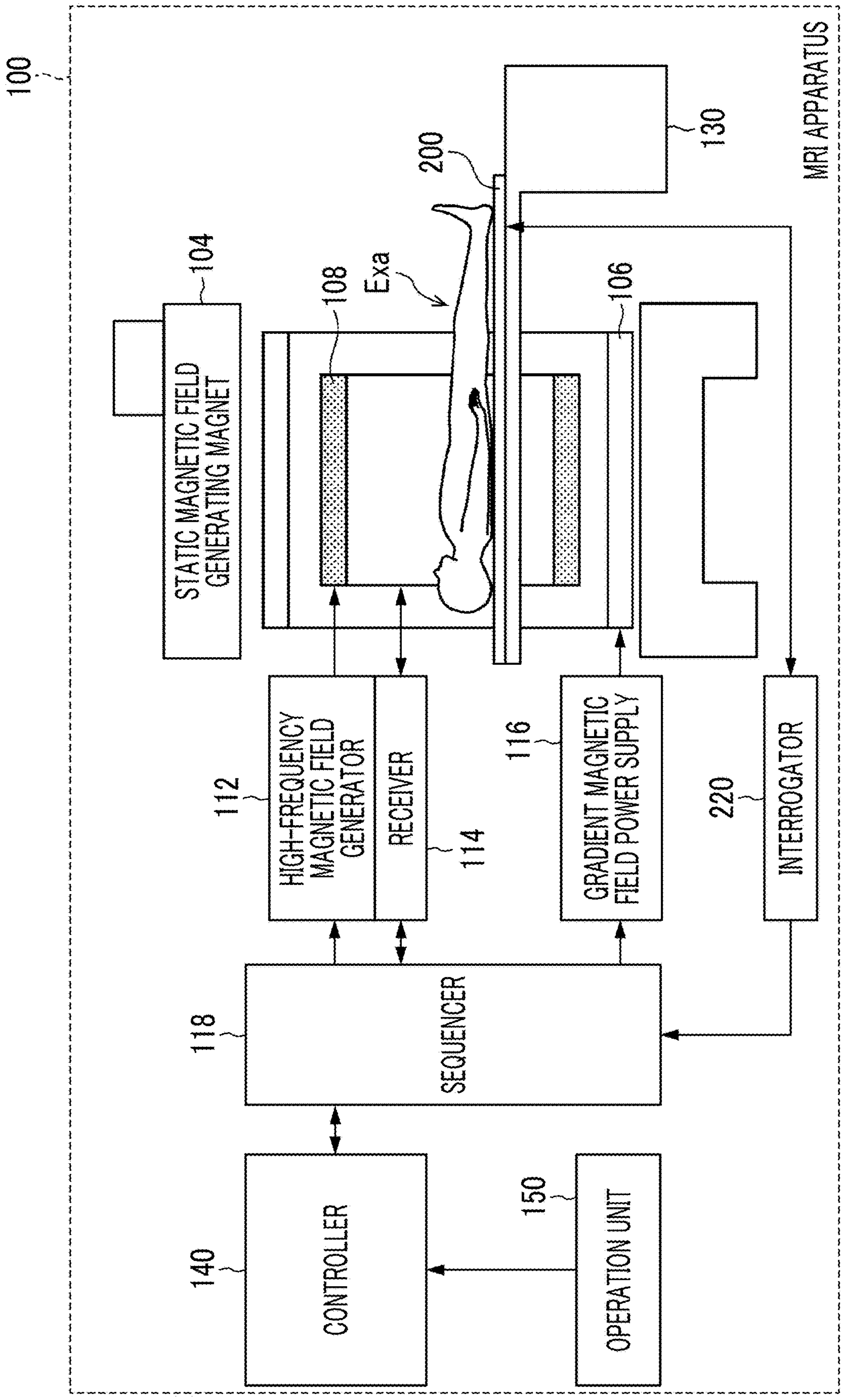
FIG. 2 is a schematic diagram showing an internal configuration of the MRI apparatus.

FIG. 2 is a schematic diagram showing an internal configuration of the MRI apparatus. The MRI apparatus 100 comprises a static magnetic field generating magnet 104, a gradient magnetic field coil 106, an RF transmission coil 108, and the sensor unit 200. RF is an abbreviation for Radio Frequency.

A subject Exa is placed on the top plate 130A of the bed 130 and is disposed in the imaging space. That is, the top plate 130A on which the subject Exa is placed is moved to the bore 120, so that an examination site of the subject Exa is moved to be located at the center of the static magnetic field in the bore 120. The reference numeral 130A of the top plate 130A is not shown in FIG. 2.

The static magnetic field generating magnet 104 generates a uniform static magnetic field in the imaging space. The static magnetic field generating magnet 104 includes a static magnetic field generating source of a permanent magnet type, a normal conduction type, or a superconducting type. The gradient magnetic field coil 106 generates a gradient magnetic field in the imaging space. The gradient magnetic field coil 106 is composed of gradient magnetic field coils in three-axis directions of X, Y, and Z, which are real space coordinate systems and stationary coordinate systems. Each gradient magnetic field coil is connected to a gradient magnetic field power supply 116 and is supplied with a current. Accordingly, the gradient magnetic field is generated in three-axis directions of X, Y, and Z.

The RF transmission coil 108 is a coil that irradiates the subject Exa with a high-frequency magnetic field pulse. The high-frequency magnetic field pulse may be referred to as an RF pulse. The RF transmission coil 108 is connected to a high-frequency magnetic field generator 112, and is supplied with a high-frequency pulse current. The high-frequency magnetic field generator 112 is driven in accordance with a command from a sequencer 118 to amplitude-modulate a high-frequency pulse, and supplies the amplified high-frequency pulse to the RF transmission coil 108.

The sequencer 118 sends commands to the high-frequency magnetic field generator 112 and the gradient magnetic field power supply 116 in accordance with the imaging sequence to generate the high-frequency magnetic field and the gradient magnetic field, respectively. The generated high-frequency magnetic field is applied to the subject Exa as a pulsed high-frequency magnetic field via the RF transmission coil 108. Accordingly, a nuclear magnetic resonance phenomenon is induced in the spins of the atoms constituting the biological tissue of the subject Exa. The nuclear magnetic resonance may be referred to as NMR using an abbreviation for nuclear magnetic resonance.

The MRI apparatus 100 comprises a receive coil unit. The receive coil unit is a coil that receives an echo signal emitted by an NMR phenomenon of the spins of atoms constituting the biological tissue of the subject Exa. The echo signal may be referred to as an NMR signal.

The receive coil unit is not shown in FIG. 2. The receive coil unit may be a blanket type, which is applied to imaging a chest and an abdomen. Different receive coil units may be applied depending on the examination site. For example, a receive coil unit for imaging various parts, such as a head, a spine, an abdomen, a leg, and an arm, can be used. The number of receive coil units used in one imaging may be one or plural, and a plurality of receive coil units for imaging different parts may be used simultaneously. The receive coil unit may be simply referred to as a receive coil. The NMR signal generated from the subject Exa is received using the receive coil unit, and the demodulation thereof is performed using a receiver 114.

The nuclear magnetic resonance frequency that is a reference for the demodulation in the receiver 114 is set by the sequencer 118. The nuclear magnetic resonance frequency may be referred to as a demodulation reference frequency. The sequencer 118 applies a pre-programmed timing and intensity and controls each unit to operate. Among programs, a program that particularly describes the timing and intensity of RF pulses, gradient magnetic fields, and signal reception is referred to as a pulse sequence. Various pulse sequences depending on the purpose are known, but the detailed description thereof will be omitted here.

The controller 140 controls the operation of the MRI apparatus 100 via the sequencer 118, receives the signal demodulated by using the receiver 114, and performs various types of signal processing such as image reconstruction.

The receiver 114 is applied with a set detection reference frequency, quadrature phase-detects an echo signal that is an analog wave, converts the echo signal into raw data, and then transmits the raw data to the controller 140. The raw data is also referred to as the echo signal or measurement data.

The sensor unit 200 detects a heartbeat of the subject Exa. The sensor unit 200 outputs a detection signal of the heartbeat of the subject Exa via an interrogator 220. The sequencer 118 monitors the heartbeat of the subject Exa based on the detection signal of the heartbeat transmitted from the interrogator 220, and performs imaging of the subject Exa.

The controller 140 can be configured by using a computer. The computer applied to the controller 140 may be a personal computer or a workstation. That is, the controller 140 comprises one or more processors and one or more memories, and the one or more processors execute a program including one or more commands stored in the one or more memories and implement various functions of the MRI apparatus 100.

The controller 140 receives various instruction inputs from an operation unit 150, collectively controls each unit of the MRI apparatus 100, and performs processing of converting the echo signal in a spatial frequency domain received via the sequencer 118 into an image in the real space by performing inverse Fourier transformation, and the like to generate an MRI image. The controller 140 is an example of a measurement data processing device that generates a medical image of the subject based on a measurement result of the subject.

The operation unit 150 includes a mouse, a keyboard, and the like, uses a display operation window of a display (not shown), and functions as a part of a GUI that receives an input of an operator using. That is, the operation unit 150 and the display function as a GUI for an operator to input the activation, the stop, the temporary stop, the pulse sequence selection, the imaging conditions, the processing conditions, and the like of the MRI apparatus 100. It should be noted that GUI is an abbreviation for Graphical User Interface.

Outline of FBG Optical Fiber

Figure 3:
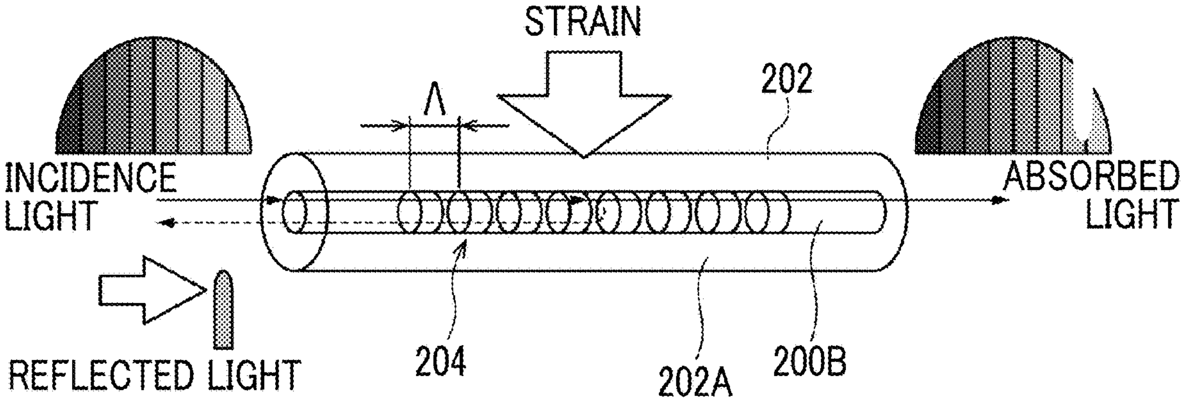
FIG. 3 is an explanatory view of an FBG optical fiber.

FIG. 3 is an explanatory view of the FBG optical fiber. The sensor unit 200 shown in FIG. 1 and the like comprises an FBG optical fiber 202. The FBG optical fiber 202 is an optical fiber type device in which a periodic refractive index change is formed in a core portion 202B of an optical fiber 202A. The refractive index change acts as a diffraction grating 204, and only light having a Bragg wavelength λ that satisfies the Bragg reflection condition based on the period of the diffraction grating 204 is reflected. In a case where a refractive index of the core is n and a grating period is Λ, the Bragg wavelength λ is represented by $\lambda=2\times n\times\Lambda$.

The diffraction grating 204 may be referred to as a fiber Bragg grating. In addition, the fiber Bragg grating may be referred to as FBG using an abbreviation for Fiber Bragg Grating in English.

The interrogator 220 shown in FIG. 2 is connected to the FBG optical fiber 202. The interrogator 220 functions as a light source device for causing incidence light to be incident on the FBG optical fiber 202 and functions as a sensor that analyzes reflected light reflected by the diffraction grating 204.

Figure 4:
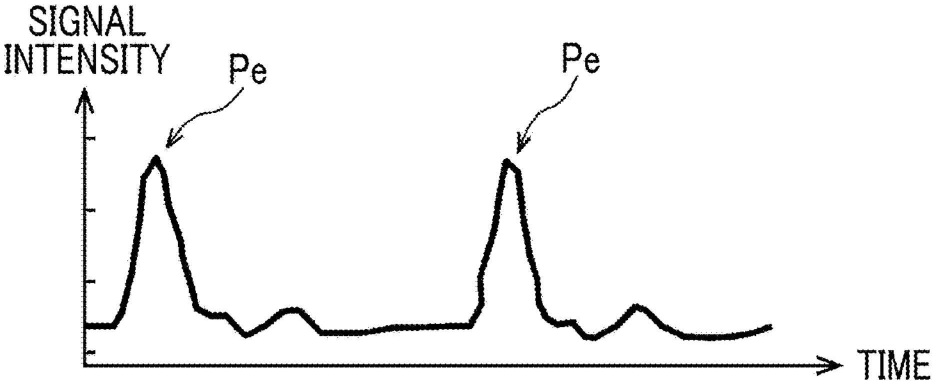
FIG. 4 is a graph showing a detection result of the FBG optical fiber.

FIG. 4 is a graph showing detection results of the FBG optical fiber. FIG. 4 shows a measurement waveform acquired as an electrical signal synchronized with the heartbeat of the subject. In the graph shown in FIG. 4, a horizontal axis is time, and a vertical axis is signal intensity.

The MRI apparatus 100 measures reflected light from the diffraction grating 204 disposed at a position close to the heart of the subject, and acquires an electrical signal indicating the strain of the FBG optical fiber 202 associated with the movement of the skin synchronized with the heartbeat of the subject. A peak Pe of the waveform shown in FIG. 4 corresponds to a ventricular systole, and the MRI apparatus 100 uses the peak Pe of the waveform as a trigger for imaging.

The FBG optical fiber 202 can detect not only pressure changes but also temperature changes. The MRI apparatus 100 has a unique problem in that a temperature in the gantry 110 rises due to the heat generation of the gradient magnetic field coil 106 and the RF transmission coil 108 during imaging. The MRI apparatus 100 comprises the FBG optical fiber for temperature detection, detects the temperature in the gantry 110 using the FBG optical fiber 202 for temperature detection, and corrects the electrical signal indicating the strain of the FBG optical fiber 202.

In addition, the MRI apparatus 100 may comprise the FBG optical fiber 202 comprising a plurality of diffraction gratings as the FBG optical fiber 202 used for monitoring the heartbeat, detect the temperature in the gantry 110 using the diffraction grating 204 at a position away from the heart of the subject, and correct the electrical signal indicating the strain of the FBG optical fiber 202. As a result, the MRI apparatus 100 can acquire the measurement waveform representing a temporal change of the detection signal synchronized with the heartbeat of the subject with high accuracy.

The FBG optical fiber 202 may comprise the plurality of diffraction gratings 204. The sensor unit 200 may automatically estimate a position of the diffraction grating 204 closest to the heart of the subject Exa from among the plurality of diffraction gratings 204 based on the captured image of a gantry camera. That is, the controller 140 of the MRI apparatus 100 may acquire the captured image of the subject Exa in which the subject Exa is imaged by using the gantry camera, analyze the captured image of the subject Exa, and estimate the position of the heart of the subject Exa. The controller 140 may notify information on the position of the diffraction grating 204 closest to the position of the heart of the subject Exa.

Figure 5:
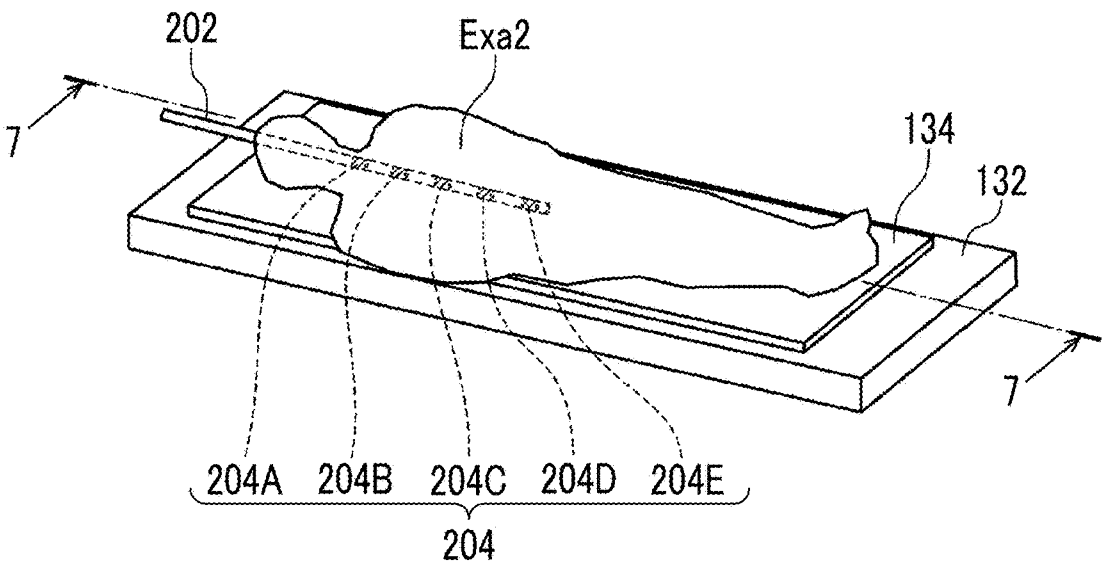
FIG. 5 is a schematic diagram of heartbeat monitoring in a subject with a large physique.
Figure 6:
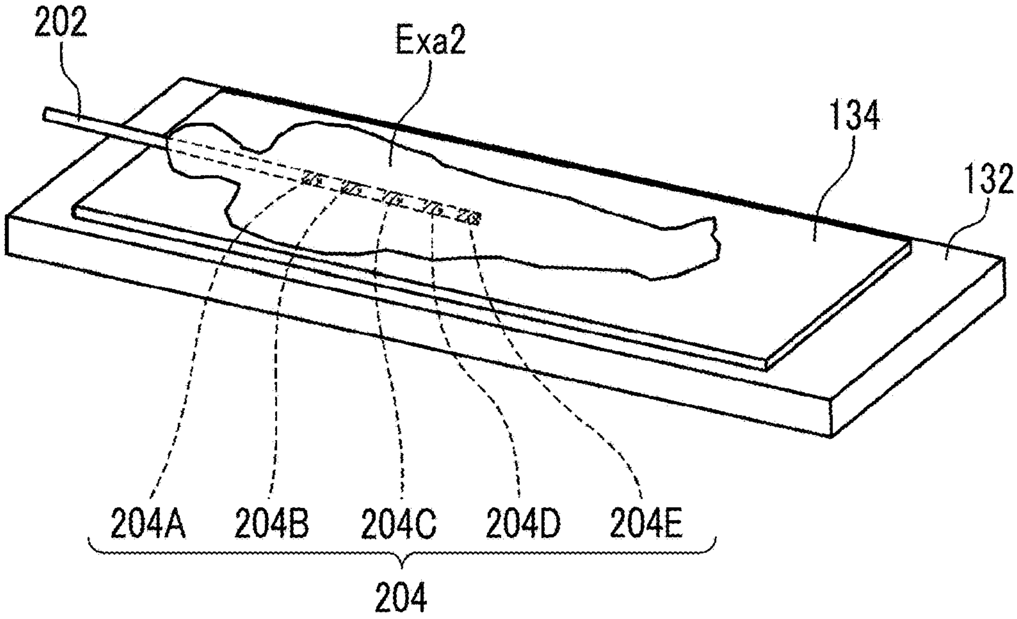
FIG. 6 is a schematic diagram of heartbeat monitoring in a subject with a small physique.

FIG. 5 is a schematic diagram of heartbeat monitoring in a subject with a large physique. In addition, FIG. 6 is a schematic diagram of heartbeat monitoring in a subject with a small physique. FIG. 5 schematically shows a state in which a subject Exa1 having a large physique is laid on a mat 134 on a table 132. Similarly, FIG. 6 schematically shows a state in which a subject Exa2 having a small physique is laid on the mat 134 on the table 132.

The FBG optical fiber 202 shown in FIG. 5 is disposed on a back side in a state where the subject Exa1 is lying on the back. The same applies to the FBG optical fiber 202 shown in FIG. 6.

The FBG optical fiber 202 shown in FIGS. 5 and 6 comprises a diffraction grating 204A, a diffraction grating 204B, a diffraction grating 204C, a diffraction grating 204D, and a diffraction grating 204E, as the plurality of diffraction gratings 204.

The subject Exa1 with a large physique shown in FIG. 5 is estimated to have the diffraction grating 204C as the diffraction grating 204 closest to the heart. The subject Exa2 with a small physique shown in FIG. 6 is estimated to have the diffraction grating 204A as the diffraction grating 204 closest to the heart.

Sensor Unit According to First Embodiment

Figure 7:
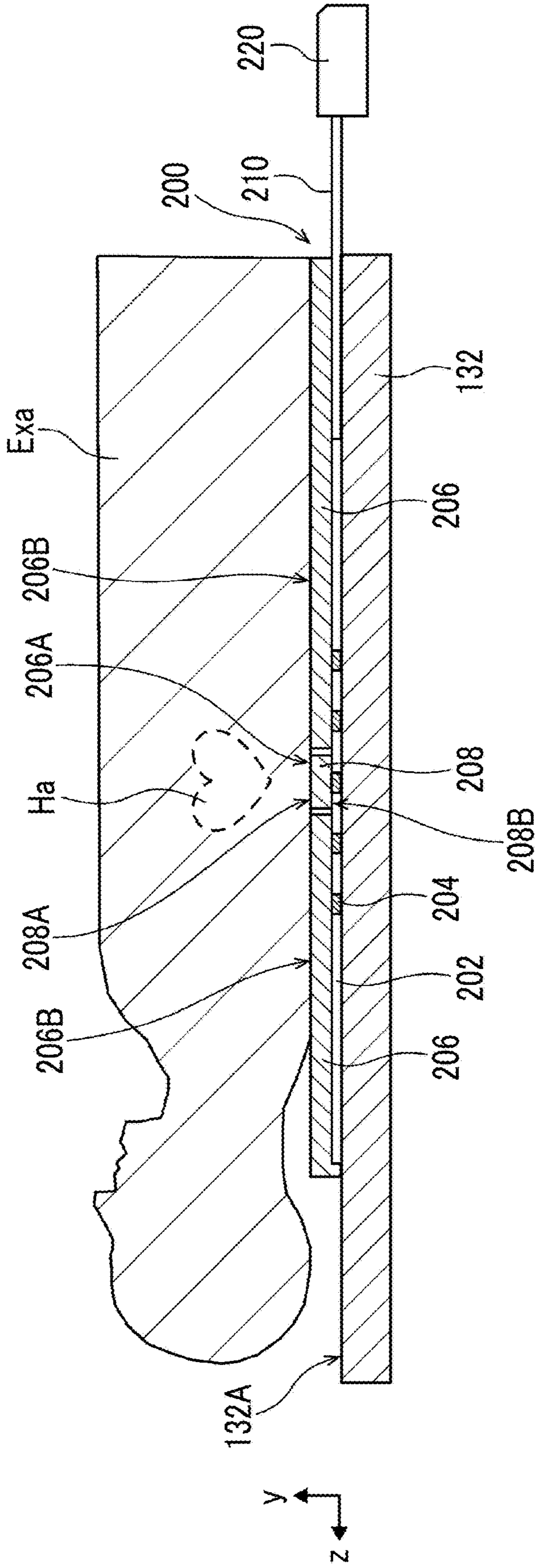
FIG. 7 is a schematic view showing a use state of a sensor unit according to a first embodiment.

FIG. 7 is a schematic view showing a use state of a sensor unit according to the first embodiment. FIG. 7 shows a cross section taken along a cross-sectional line 7-7 shown in FIG. 5. For convenience of illustration, in FIG. 7, the cross-sectional line is omitted as appropriate.

The sensor unit 200 shown in FIG. 7 comprises the FBG optical fiber 202, the diffraction grating 204, a weight prevention cover 206, and a heartbeat propagation tool 208. The interrogator 220 is connected to the FBG optical fiber 202 via an optical fiber 210. The optical fiber 210 functions as a propagation path for incidence light and a propagation path for reflected light between the FBG optical fiber 202 and the interrogator 220.

Each of a y direction and a z direction shown in FIG. 7 is one direction in a three-dimensional orthogonal coordinate system applied to a three-dimensional space in which the MRI apparatus 100 is installed. The y direction is an axis orthogonal to a surface on which the MRI apparatus 100 is installed. The y direction may be a vertical direction. The z direction may be a direction parallel to a surface on which the MRI apparatus 100 is installed and parallel to a longitudinal direction of the table 132. The x direction, which is not shown in FIG. 7, is a direction orthogonal to the y direction and the z direction, and may be a direction parallel to a lateral direction of the table 132.

The FBG optical fiber 202 is installed on an upper surface 132A of the table 132 of the MRI apparatus 100. That is, the FBG optical fiber 202 is fixed to a hard object having a predetermined stiffness on a side opposite to a side facing the subject Exa. As a result, the FBG optical fiber 202 is suppressed from moving from a position fixed in the three-dimensional space, and thus the drift of the measurement waveform is suppressed.

The heartbeat of the subject Exa is applied with a small strain of several micrometers to several hundred micrometers with respect to the FBG optical fiber 202 in the y direction. The FBG optical fiber 202 detects the small strain as a heartbeat. The sensor unit 200 outputs a measurement waveform representing the temporal change in the heartbeat as a detection result of the FBG optical fiber 202.

On the other hand, in a case where the subject Exa moves in an unpredictable manner, such as moving the hands and feet, the FBG optical fiber 202, which is not fixed and moves in the three-dimensional space, moves by several hundred micrometers to several millimeters in the x direction and the z direction. As a result, the measurement waveform drifts.

The sensor unit 200 has a structure in which the weighting caused by the movement of the subject with respect to the FBG optical fiber 202 and the optical fiber 210 is suppressed. That is, the FBG optical fiber 202 and the optical fiber 210 are covered with the weight prevention cover 206 on a side facing the subject Exa. As a result, the drift of the measurement waveform caused by unpredictable movements of the hands and feet of the subject is suppressed.

A material having a predetermined stiffness is applied to the weight prevention cover 206. Examples of the material of the weight prevention cover 206 include a synthetic resin such as plastic. The stiffness of the weight prevention cover 206 may be equal to or less than the stiffness of the upper surface 132A of the table 132.

The weight prevention cover 206 has a structure that covers the entire length of the FBG optical fiber 202 in a direction in which the FBG optical fiber 202 extends. The weight prevention cover 206 may have a structure that covers a part or the entire length of the optical fiber 210 connected to the FBG optical fiber 202 in the direction in which the FBG optical fiber 202 extends.

The heartbeat propagation tool 208 is installed at a position where one surface 208A comes into contact with a lower portion of a heart Ha on the back side of the subject Exa and the other surface 208B is in contact with the diffraction grating 204 of the FBG optical fiber 202. In the weight prevention cover 206, a cover hole 206A that penetrates in the y direction is formed at a position where the heartbeat propagation tool 208 is installed.

The heartbeat propagation tool 208 propagates the movement of the subject Exa synchronized with the heartbeat of the subject Exa, which is the purpose of measurement, to the diffraction grating 204 of the FBG optical fiber 202 with high-sensitivity. Accordingly, it is possible to monitor the heartbeat of the subject Exa while the subject Exa is still wearing the clothes.

For the position in the y direction with reference to the upper surface 132A of the table 132, a position of the surface of the heartbeat propagation tool 208 that comes into contact with the subject Exa is higher than a position of the one surface 206B of the weight prevention cover 206. That is, the heartbeat propagation tool 208 has a structure in which one surface 208A protrudes in the y direction from the cover hole 206A that penetrates the weight prevention cover 206.

A material softer than the weight prevention cover 206 is used for the heartbeat propagation tool 208. An example of a material applied to the heartbeat propagation tool 208 is rubber. The stiffness of the heartbeat propagation tool 208 may be less than the stiffness of the weight prevention cover 206.

The heartbeat propagation tool 208 shown in FIG. 7 has a shape in which a length of the surface that comes into contact with the subject Exa in the z direction is the same as a length of the surface that comes into contact with the diffraction grating 204. The heartbeat propagation tool 208 may have the same length as the diffraction grating 204 in the z direction, or may have a length equal to or longer than the length of the diffraction grating 204. Here, the term "same" in the present specification is not limited to a completely matching aspect but may include substantially the same aspects that differ yet achieve similar functions and effects.

The table 132 is an example of a fixing member that is also used as a table on which the subject of the present disclosure is placed. The FBG optical fiber 202 is an example of a fiber Bragg grating sensor according to the present disclosure. The diffraction grating 204 is an example of one or more sensor elements according to the present disclosure. The weight prevention cover 206 is an example of a cover according to the present disclosure. The heartbeat propagation tool 208 is an example of a contact assisting member according to the present disclosure.

Figure 8:
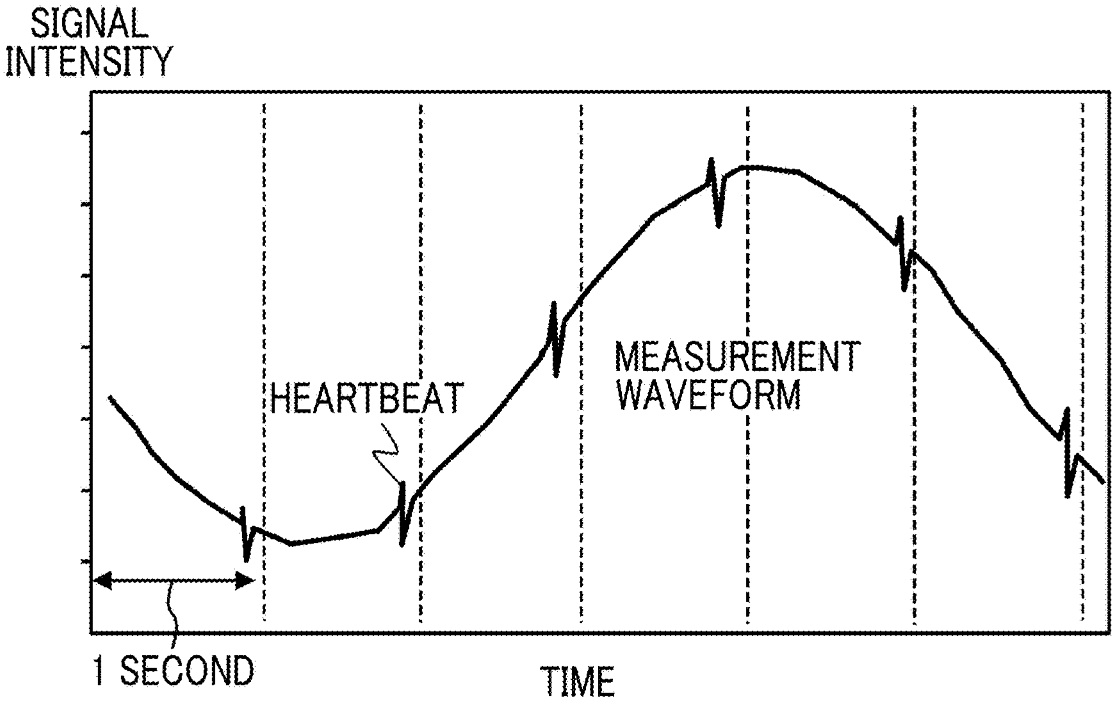
FIG. 8 is a graph showing an electrocardiographic waveform acquired using the sensor unit according to the first embodiment.

FIG. 8 is a graph showing an electrocardiographic waveform acquired using the sensor unit according to the first embodiment. In the graph shown in FIG. 8, a horizontal axis is time, and a vertical axis is signal intensity. The signal intensity is normalized.

The measurement waveform shown in FIG. 8 is synchronized with breathing, with a long period waveform of approximately 6 seconds, on which a short period waveform synchronized with the heartbeat is superimposed. The waveform of the long period can be separated from the measurement waveform using a frequency filter and can be removed from the measurement waveform.

The MR signal is measured while being synchronized with the heartbeat based on the heartbeat waveform extracted from the measurement waveform. As a result, it is possible to capture a still image of each time phase of a heartbeat of the subject Exa.

Figure 9:
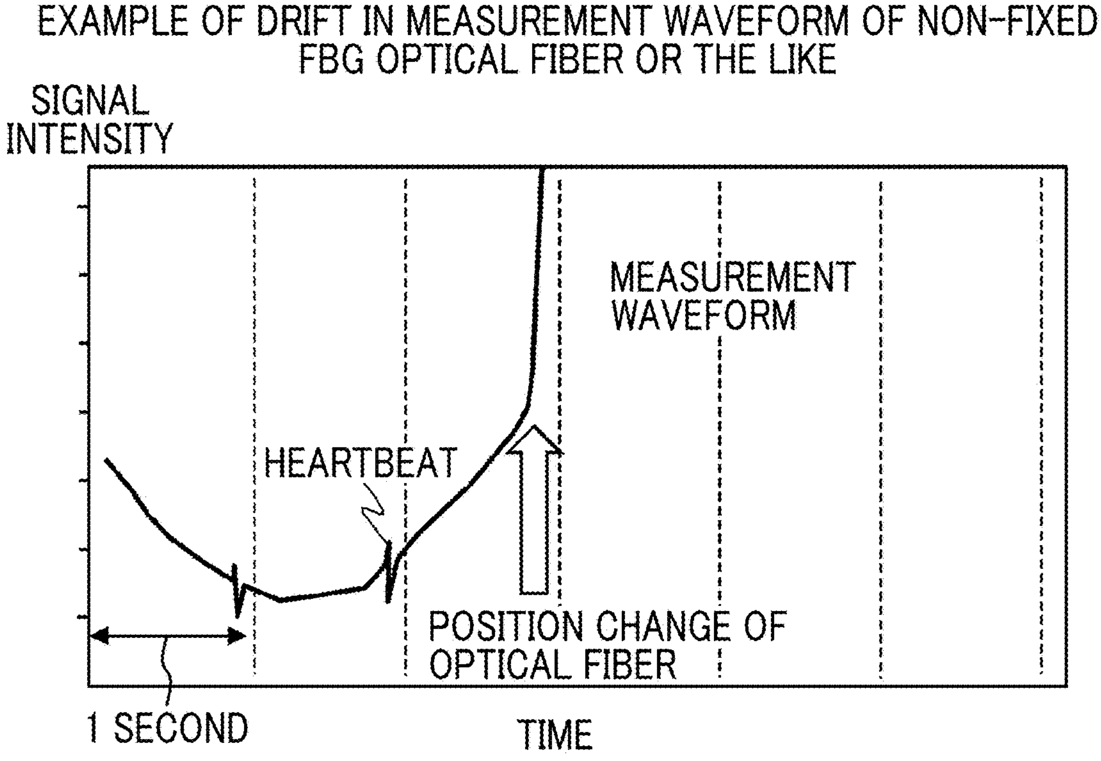
FIG. 9 is a graph showing a measurement waveform in a case where drift occurs.

FIG. 9 is a graph showing a measurement waveform in a case where drift occurs. FIG. 9 shows an example of the drift in the measurement waveform of a non-fixed FBG optical fiber or the like. In the graph shown in FIG. 9, a horizontal axis is time, and a vertical axis is signal intensity. The signal intensity is normalized.

In a case where a position of the non-fixed FBG optical fiber 202 or the like is changed at a timing indicated by an arrow line, as shown in FIG. 9, drift occurs in the measurement waveform. In a case where the drift occurs in the measurement waveform, it is difficult to measure the heartbeat for several seconds until zero correction is completed at the position where the FBG optical fiber 202 or the like is stopped.

Sensor Unit According to Second Embodiment

Figure 10:
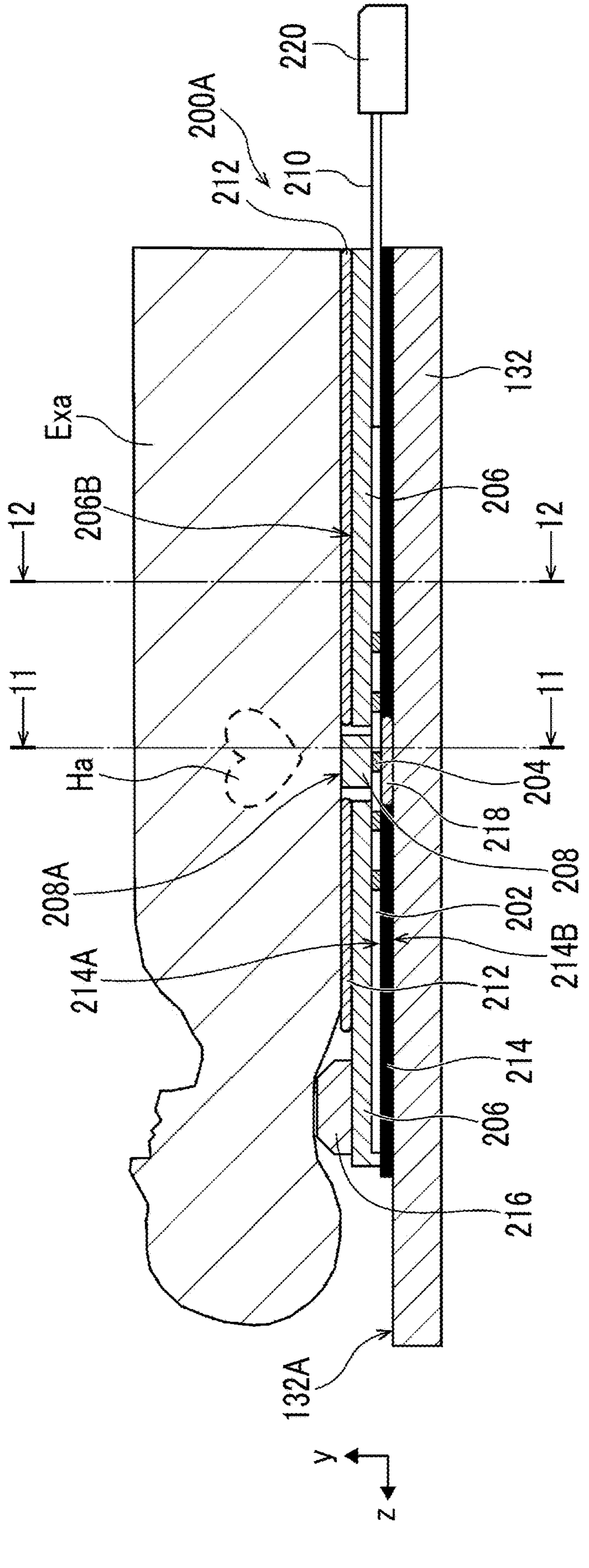
FIG. 10 is a schematic view showing a use state of a sensor unit according to a second embodiment.

FIG. 10 is a schematic view showing a use state of the sensor unit according to the second embodiment. In the following, mainly, the difference from the sensor unit 200 according to the first embodiment will be described.

A sensor unit 200A according to the second embodiment has a detachable structure that allows the sensor unit 200A to be attached to and detached from the table 132. In a case where the MRI apparatus 100 does not perform the cardiac-gated imaging, there is a need to detach the sensor unit 200A. Therefore, the sensor unit 200A comprises a rigid member 214 having a shape following the shape of the upper surface 132A of the table 132, and is configured to be freely attachable to and detachable from the table 132.

That is, the FBG optical fiber 202 is fixed to one surface 214A of the rigid member 214 in the sensor unit 200A. The other surface 214B of the rigid member 214 is fixed to the upper surface 132A of the table 132 in the sensor unit 200A, and the sensor unit 200A is integrated with the table 132. Accordingly, the sensor unit 200A obtains the same effect as in a case where the FBG optical fiber 202 is fixed to the upper surface 132A of the table 132.

In addition, the sensor unit 200A comprises a mat 212 and a neck rest 216. The mat 212 and the neck rest 216 are installed on the one surface 214A of the rigid member 214.

The mat 212 and the neck rest 216 have a structure in which a height in the y direction, based on the one surface 214A of the rigid member 214, is constant. For the mat 212 and the neck rest 216, a material that is elastically deformed in a case where the subject Exa is placed thereon may be applied.

The mat 212 is disposed at a position corresponding to a position of a body of the subject Exa in the z direction. The neck rest 216 is disposed at a position corresponding to a position of a neck of the subject Exa in the z direction.

A material having a stiffness lower than the stiffness of the heartbeat propagation tool 208 is applied to the mat 212. For the mat 212, a material that is elastically deformed in a case where the subject Exa is placed thereon may be applied. The same material as the mat 212 may be applied to the neck rest 216.

The mat 212 and the neck rest 216 have a structure in which a height in the y direction, based on the one surface 214A of the rigid member 214, is constant. That is, a surface of the mat 212 that comes into contact with the subject Exa and a surface of the neck rest 216 that comes into contact with the subject Exa are planes that are parallel to the one surface 214A of the rigid member 214.

For the position in the y direction with reference to the one surface 214A of the rigid member 214, a position of the surface of the mat 212 on the side where the subject Exa contacts is higher than the position of the one surface 206B of the weight prevention cover 206.

In addition, for the position in the y direction with reference to the one surface 214A of the rigid member 214, a position of one surface 208A of the heartbeat propagation tool 208 is higher than the position of the surface of the mat 212 on the side where the subject Exa contacts.

Further, the sensor unit 200A comprises a buffer member 218. The buffer member 218 is located at a position where the diffraction grating 204 is formed, and is installed between the FBG optical fiber 202 and the rigid member 214. FIG. 10 shows the buffer member 218 that is embedded in the rigid member 214.

Figure 11:
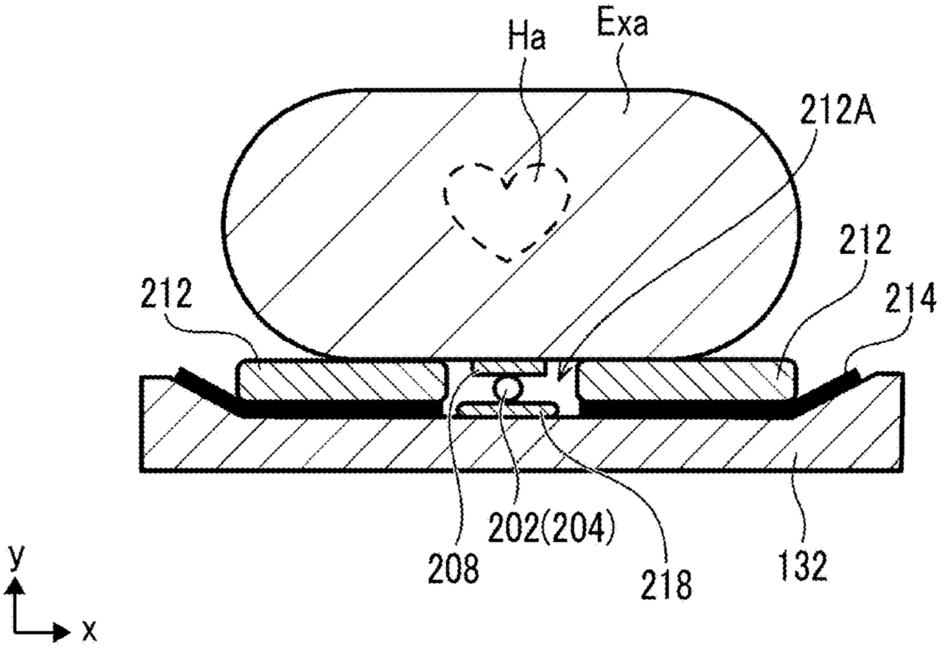
FIG. 11 is a cross-sectional view taken along a cross-sectional line 11-11 in FIG. 10.

FIG. 11 is a cross-sectional view taken along a cross-sectional line 11-11 in FIG. 10. FIG. 11 schematically shows a structural example at the position of the diffraction grating 204 of the FBG optical fiber 202 shown in FIG. 10.

The mat 212 is installed on both sides of the FBG optical fiber 202 in the x direction. In the mat 212, a through hole 212A is formed at a position in the xy plane corresponding to the position of the diffraction grating 204. That is, one surface 208A of the heartbeat propagation tool 208 protrudes from the mat 212. As a result, it is possible to reliably bring the one surface 208A of the heartbeat propagation tool 208 into contact with the subject Exa.

Figure 12:
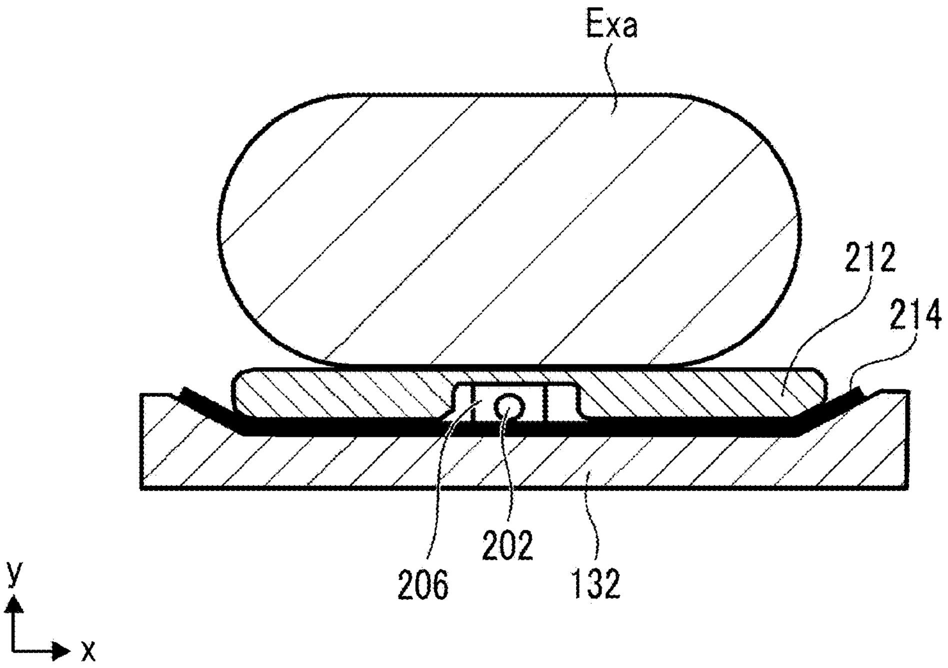
FIG. 12 is a cross-sectional view taken along a cross-sectional line 12-12 in FIG. 10.

FIG. 12 is a cross-sectional view taken along a cross-sectional line 12-12 in FIG. 10. FIG. 12 schematically shows a structural example of the FBG optical fiber 202 shown in FIG. 10 at a position where the diffraction grating 204 is not formed. The mat 212 is installed on both sides of the FBG optical fiber 202 in the x direction, and the mat 212 is also installed on an upper side of the weight prevention cover 206.

That is, at the position where the diffraction grating 204 is not formed, the weight prevention cover 206 is covered with the mat 212. As a result, the contact of the weight prevention cover 206 with the subject Exa is prevented, a hard feeling that the subject Exa feels on the back is alleviated, and the subject Exa can relax.

Further, the sensor unit 200A comprises the buffer member 218. The buffer member 218 is installed at a position between the diffraction grating 204 and the rigid member 214. In a case of comprising the buffer member 218, the hard feeling that the subject Exa feels on the back is alleviated, and the subject Exa can relax. The buffer member 218 may be joined to the position of the diffraction grating 204 of the FBG optical fiber 202. In the rigid member 214, a through hole, a recess, or the like corresponding to a shape of the buffer member 218 may be formed at a position where the buffer member 218 is installed.

The rigid member 214 is an example of a fixing member according to the present disclosure. The buffer member 218 is an example of a first elastic member having predetermined elasticity in the present disclosure. The mat 212 is an example of a second elastic member according to the present disclosure.

Sensor Unit According to Third Embodiment

Figure 13:
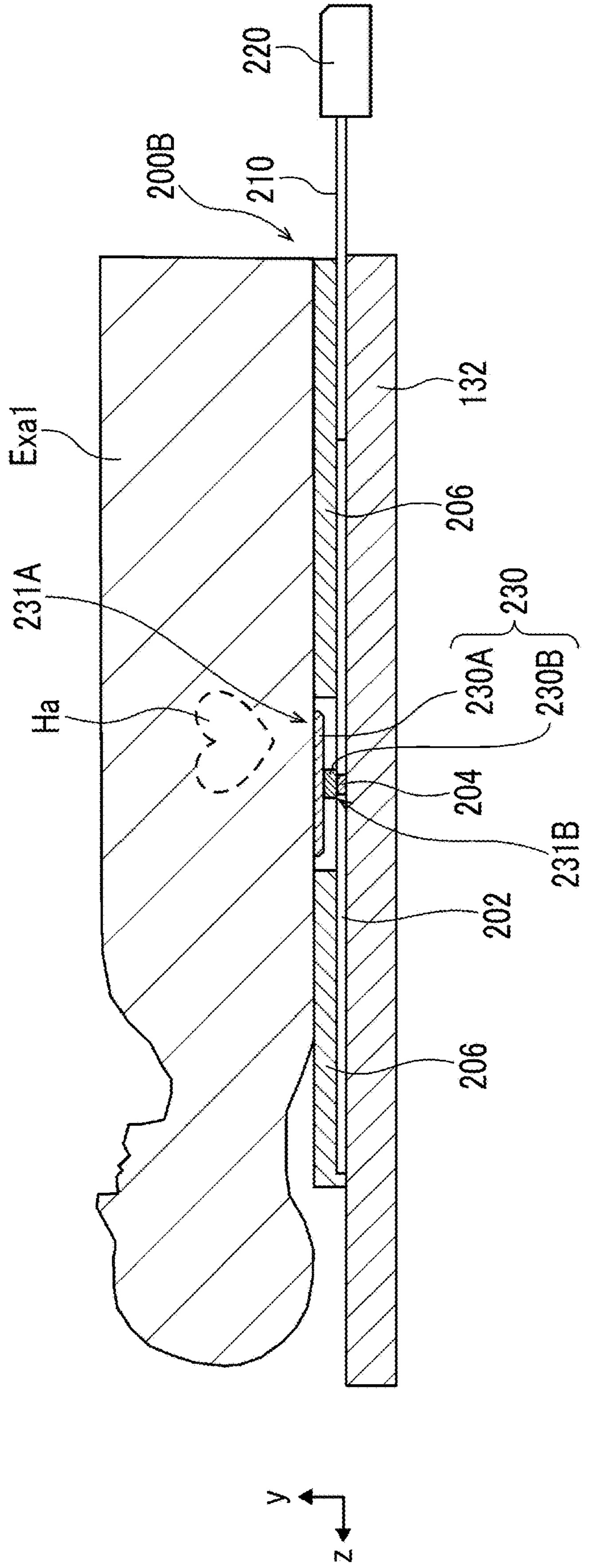
FIG. 13 is a schematic view showing a use state of a sensor unit according to a third embodiment.

FIG. 13 is a schematic view showing a use state of the sensor unit according to the third embodiment. In the following, mainly, the difference from the sensor unit 200 according to the first embodiment will be described. A sensor unit 200B according to the third embodiment comprises a heartbeat propagation tool 230 having a structure different from that of the heartbeat propagation tool 208 shown in FIG. 7.

The heartbeat propagation tool 230 comprises a subject contact portion 230A that comes into contact with the subject Exa1 and a fiber contact portion 230B that comes into contact with the diffraction grating 204. In the heartbeat propagation tool 230, an area of a first surface 231A to be brought into contact with the subject Exa1 or the like in the subject contact portion 230A is larger than an area of a second surface 231B to be brought into contact with the diffraction grating 204 of the fiber contact portion 230B. Specifically, a length of the subject contact portion 230A in the z direction is a length in the z direction from a position of the heart Ha of the large subject Exa1 to a position of the heart Ha of the small subject Exa2. The z direction is an example of a longitudinal direction of the bed according to the present disclosure.

Figure 14:
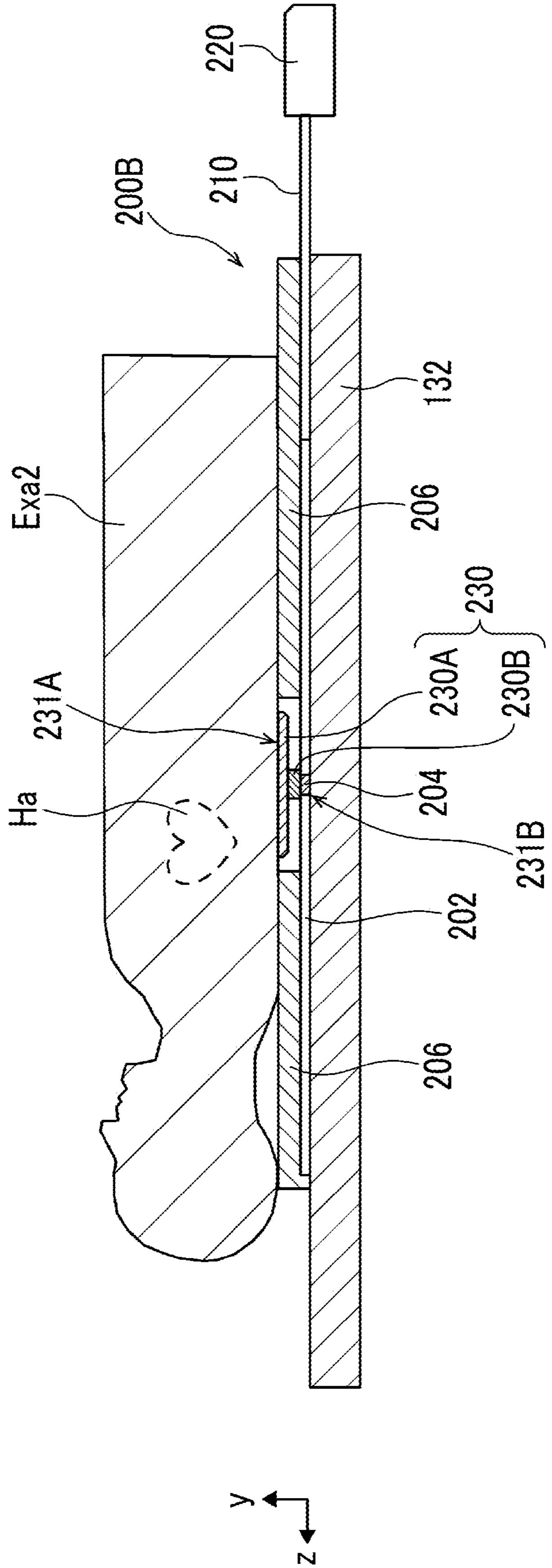
FIG. 14 is a schematic diagram showing a use state of the sensor unit in a subject with a small physique.

FIG. 14 is a schematic diagram showing a use state of the sensor unit in the subject with a small physique. The sensor unit 200B can bring the subject contact portion 230A of the heartbeat propagation tool 230 into contact with the position on the back side corresponding to the position of the heart Ha even in a case of the subject Exa2 with a small physique.

As a result, the variation in the position of the heart Ha from the small subject Exa2 to the large subject Exa1 can be housed using one diffraction grating 204, and the workflow can be improved.

Structural Example of Weight Prevention Cover

First Structural Example

Figure 15:
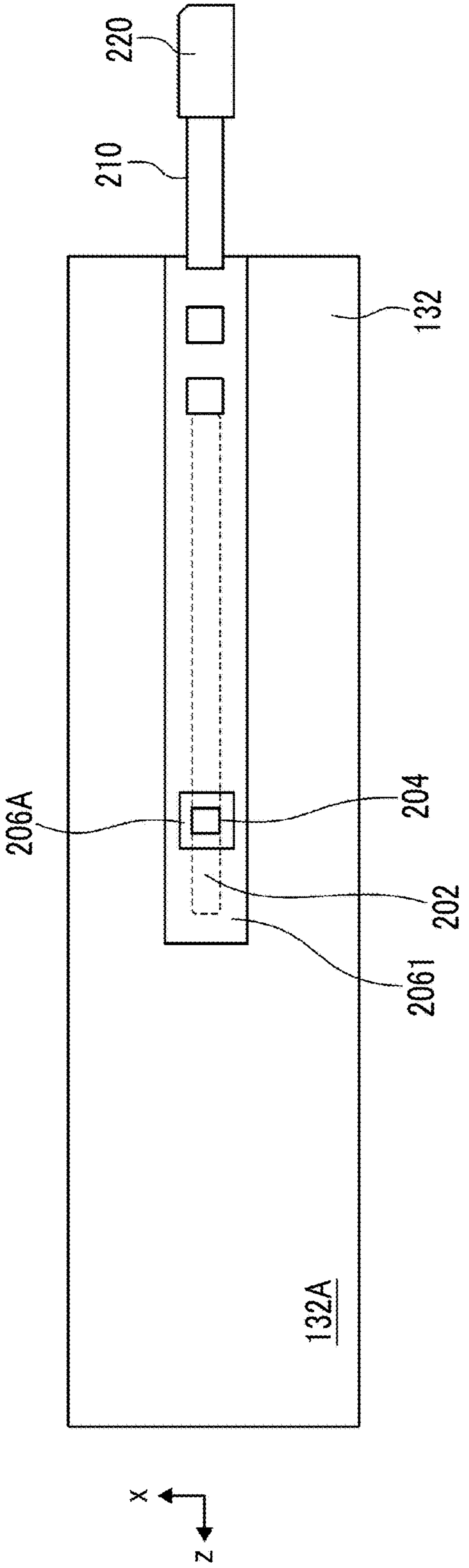
FIG. 15 is a plan view of a weight prevention cover according to a first structural example.

FIG. 15 is a plan view of a weight prevention cover according to the first structural example. A weight prevention cover 2061 shown in FIG. 15 has a rod-like structure extending in the z direction, which is a longitudinal direction of the table 132.

The weight prevention cover 2061 according to the first structural example is hardly affected by the movement of the hands and feet of the subject Exa. In addition, the FBG optical fiber 202 comprising one diffraction grating 204 is shown in FIG. 15. The same applies to FIGS. 16 and 17.

Second Structural Example

Figure 16:
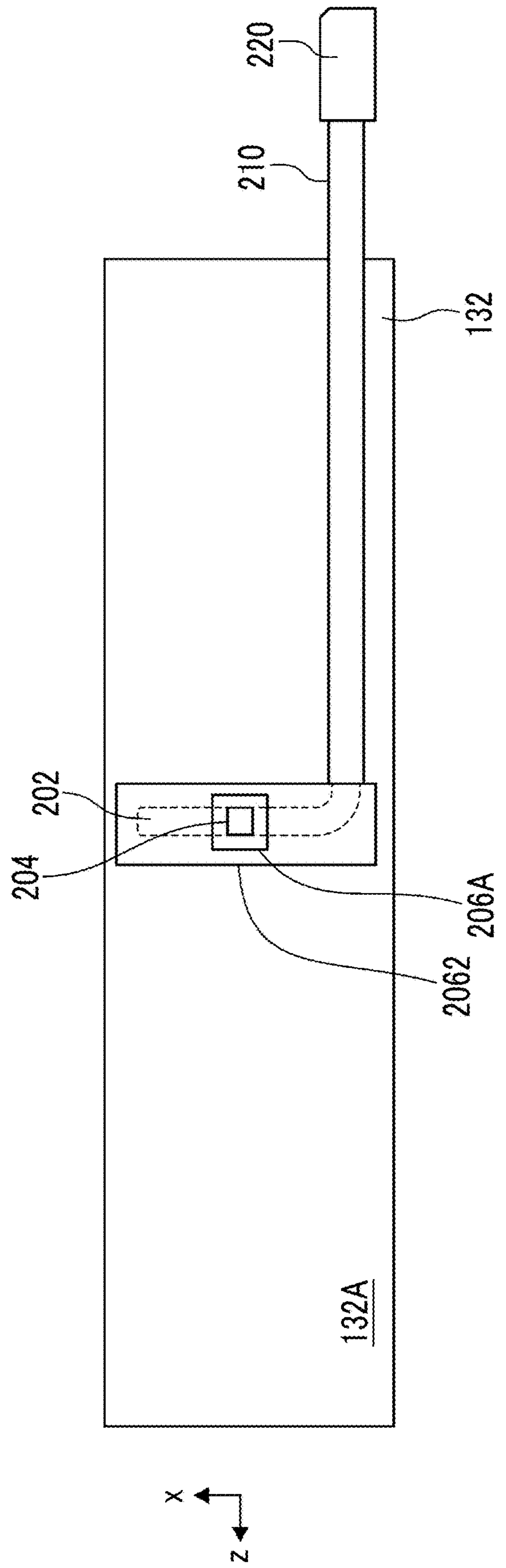
FIG. 16 is a plan view of a weight prevention cover according to a second structural example.

FIG. 16 is a plan view of a weight prevention cover according to the second structural example. A weight prevention cover 2062 shown in FIG. 16 has a rod-like structure extending in the x direction, which is a lateral direction of the table 132.

In the case of the weight prevention cover 2062 according to the second structural example, most of the optical fiber 210 connected to the FBG optical fiber 202 can be installed at an end of the table 132 where the weight of the subject Exa is not applied, and a length of the weight prevention cover 2062 in the z direction can be relatively shortened.

Third Structural Example

Figure 17:
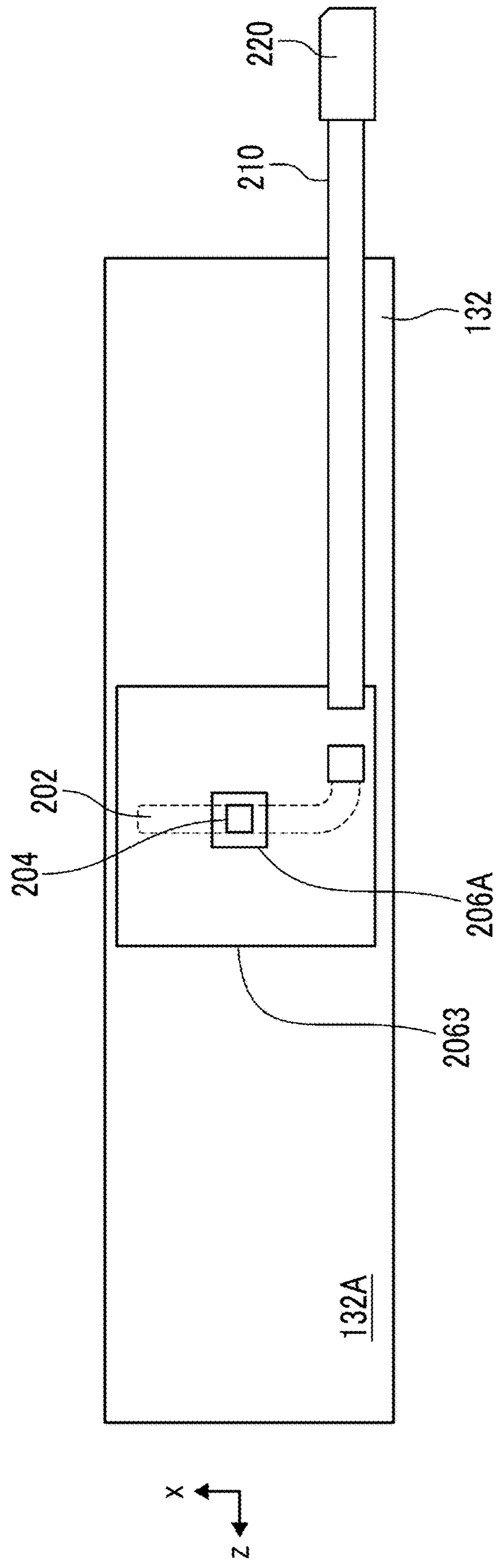
FIG. 17 is a plan view of a weight prevention cover according to a third structural example.

FIG. 17 is a plan view of a weight prevention cover according to the third structural example. A weight prevention cover 2063 shown in FIG. 17 has a planar structure having a predetermined length in the x direction and the z direction. FIG. 17 shows the weight prevention cover 2063 having a square planar shape in the xz plane, but the planar shape of the weight prevention cover 2063 in the xz plane may be a quadrangular shape such as a rectangle or a parallelogram, a polygonal shape such as a regular polygon, a circle, an ellipse, or the like.

The size of the weight prevention cover 2063 may be any size as long as the FBG optical fiber 202 and the optical fiber 210 are covered in a region on which the subject Exa is placed.

In the case of the weight prevention cover 2063 according to the third structural example, similar to the weight prevention cover 2062 according to the second structural example, most of the optical fiber 210 can be installed at the end of the table 132, and the length of the weight prevention cover 2062 in the z direction can be relatively shortened.

FIGS. 15 to 17 show the cover hole 206A having a square planar shape in the xz plane, but the planar shape of the cover hole 206A in the xz plane may be a quadrangular shape such as a rectangle and a parallelogram, or a polygonal shape, a circle, an ellipse, or the like.

Fourth Structural Example

Figure 18:
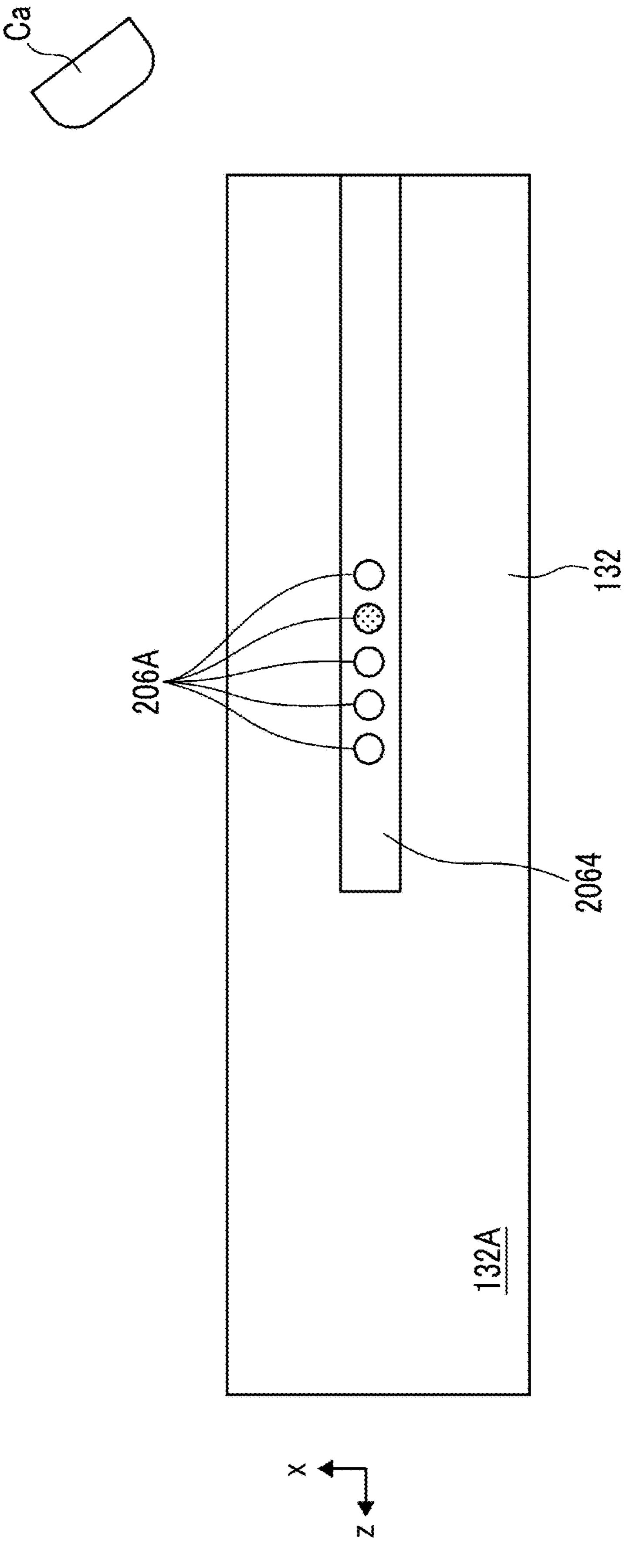
FIG. 18 is a plan view of a weight prevention cover according to a fourth structural example.

FIG. 18 is a plan view of a weight prevention cover according to the fourth structural example. In FIG. 18, the FBG optical fiber 202, the optical fiber 210, the interrogator 220, and the like are not shown. The same applies to FIG. 19.

A weight prevention cover 2064 shown in FIG. 18 is formed with a plurality of cover holes 206A along the z direction. A position of each of the plurality of cover holes 206A in the xz plane corresponds to a position of each of the plurality of diffraction gratings 204 formed on the FBG optical fibers 202 in the xz plane.

In the sensor unit 200 comprising the weight prevention cover 2064 in which the plurality of cover holes 206A corresponding to the position of each of the plurality of diffraction gratings 204 are formed, the diffraction grating 204 closest to the position of the heart Ha of the subject Exa is selected, and the heartbeat propagation tool 208 is attached to the selected diffraction grating 204. In FIG. 18, the cover hole 206A corresponding to the selected diffraction grating 204 is marked with a dot hatch.

The position of the heart Ha of the subject Exa can be grasped based on the analysis results of the captured image obtained by imaging the subject Exa using the camera Ca such as a gantry camera.

In the sensor unit 200 comprising the weight prevention cover 2064 according to the fourth structural example, the heartbeat of the subject Exa is propagated to the diffraction grating 204 with high-sensitivity. In addition, in the diffraction grating 204 corresponding to the cover hole 206A to which the heartbeat propagation tool 208 is not attached, the weight caused by the movement of the subject Exa is not transmitted, and the occurrence of the drift of the detection waveform caused by the unpredictable movement of the subject Exa is suppressed.

Further, it is possible to cover the variation in the position of the heart Ha from the small subject Exa2 to the large subject Exa1 by using the position of the neck rest 216 shown in FIG. 10 as the reference position. For example, in the z direction, in a case where the five cover holes 206A are formed with a disposition pitch of 5 centimeters, it is possible to correspond to the subject Exa having a height of 1.2 meters to 2.0 meters.

Fifth Structural Example

Figure 19:
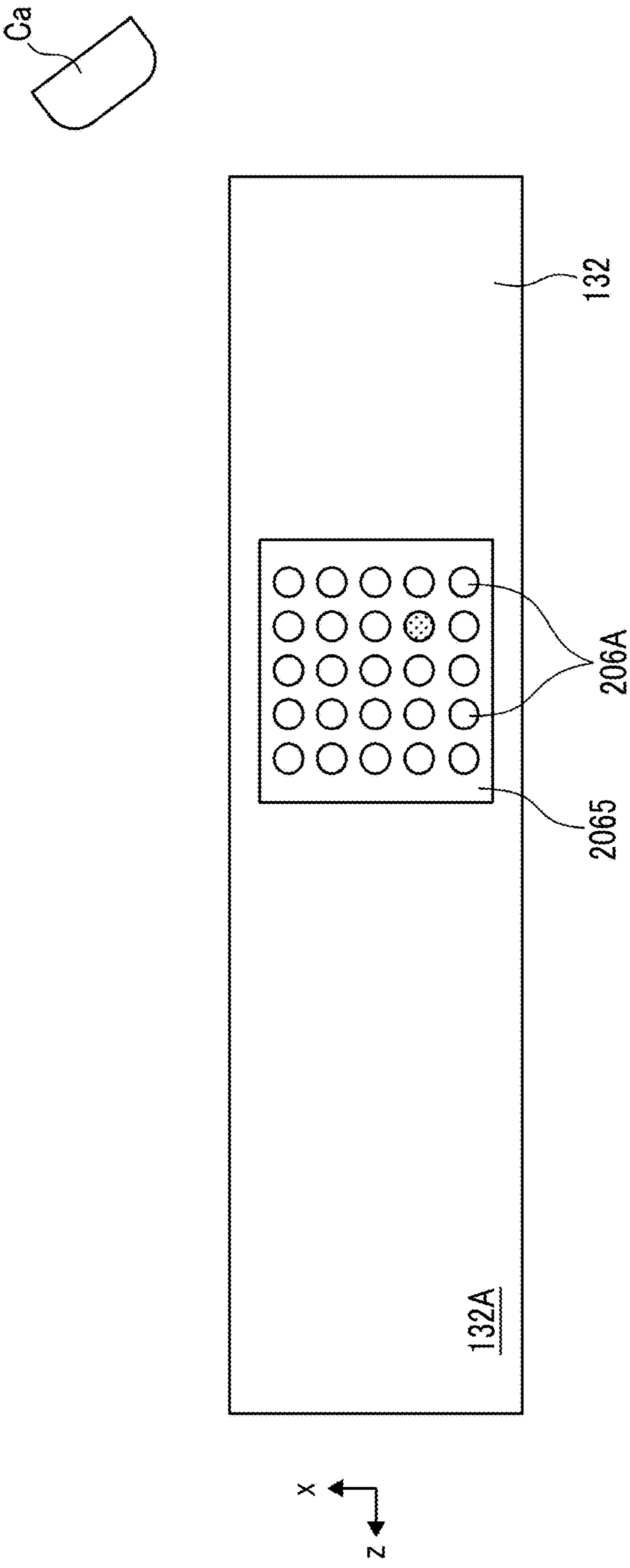
FIG. 19 is a plan view of a weight prevention cover according to a fifth structural example.

FIG. 19 is a plan view of a weight prevention cover according to the fifth structural example. In a weight prevention cover 2065 according to the fifth structural example, a plurality of cover holes 206A are formed along each of the x direction and the z direction.

In the sensor unit 200 comprising the weight prevention cover 2065, the diffraction grating 204 closest to the position of the heart Ha of the subject Exa is selected, and the heartbeat propagation tool 208 is attached to the selected diffraction grating 204. In FIG. 19, the cover hole 206A corresponding to the selected diffraction grating 204 is marked with a dot hatch.

The sensor unit 200 comprising the weight prevention cover 2065 can obtain the same effects as the sensor unit 200 comprising the weight prevention cover 2064 according to the fourth structure example. In addition, the sensor unit 200 comprising the weight prevention cover 2065 has a wider selection range of the diffraction grating 204 compared to the sensor unit 200 comprising the weight prevention cover 2064 according to the fourth structural example.

Use Example of FBG Optical Fiber

Figure 20:
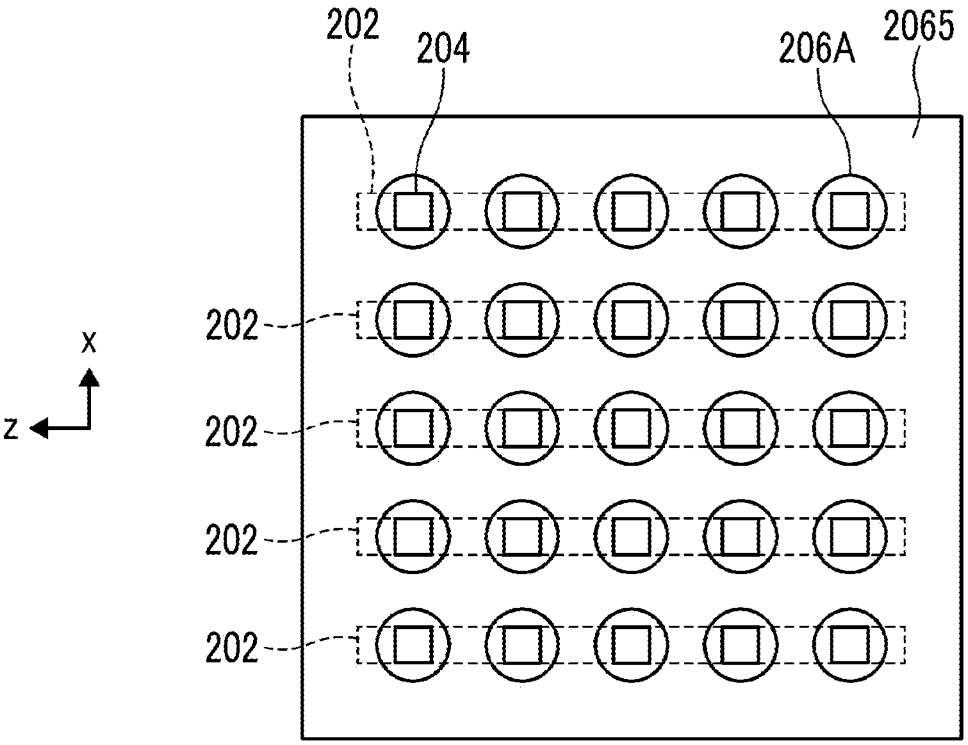
FIG. 20 is a schematic view showing a first use example of the FBG optical fiber in a case where the weight prevention cover according to the fifth structural example is applied.

FIG. 20 is a schematic view showing a first use example of the FBG optical fiber in a case where the weight prevention cover according to the fifth structural example is applied. In the weight prevention cover 2065 in which the plurality of cover holes 206A are formed in a two-dimensional shape, the plurality of FBG optical fibers 202 are used.

FIG. 20 shows an aspect in which five FBG optical fibers 202 extending in the z direction are installed along the x direction. In FIG. 20, the optical fiber 210, the interrogator 220, and the like are not shown. The same applies to FIGS. 21 and 22.

Figure 21:
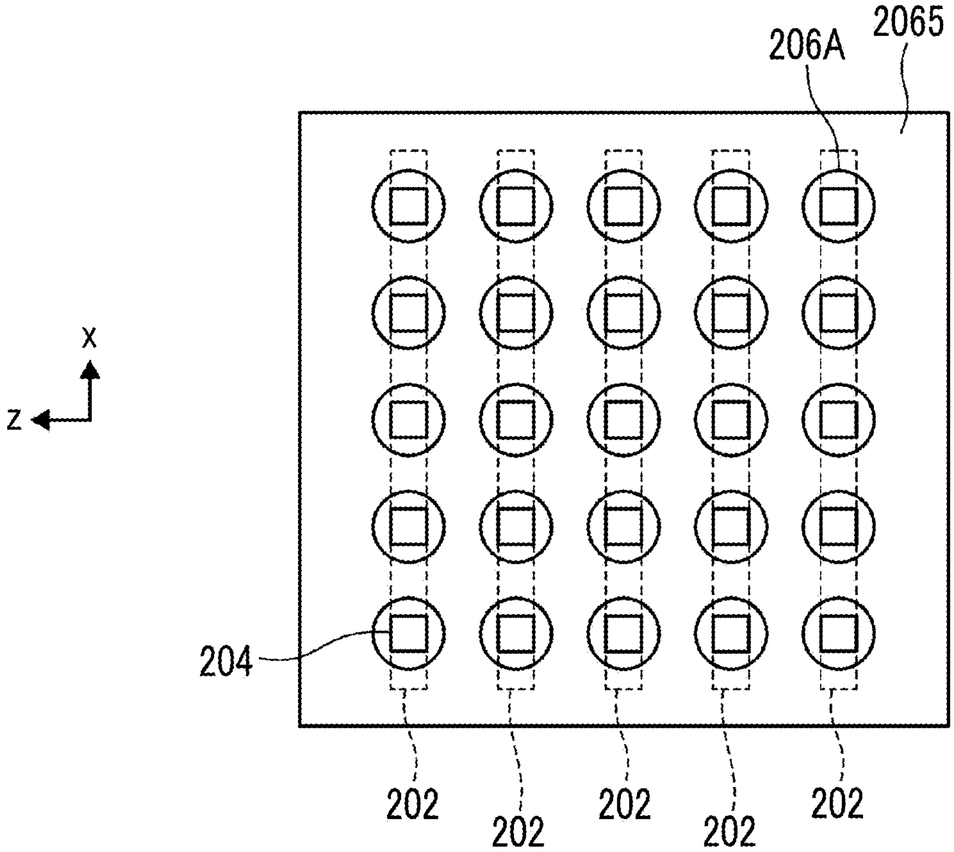
FIG. 21 is a schematic view showing a second use example of the FBG optical fiber in a case where the weight prevention cover is applied according to the fifth structural example.

FIG. 21 is a schematic view showing a second use example of the FBG optical fiber in a case where the weight prevention cover is applied according to the fifth structural example. FIG. 21 shows an aspect in which five FBG optical fibers 202 extending in the x direction are installed along the z direction.

Figure 22:
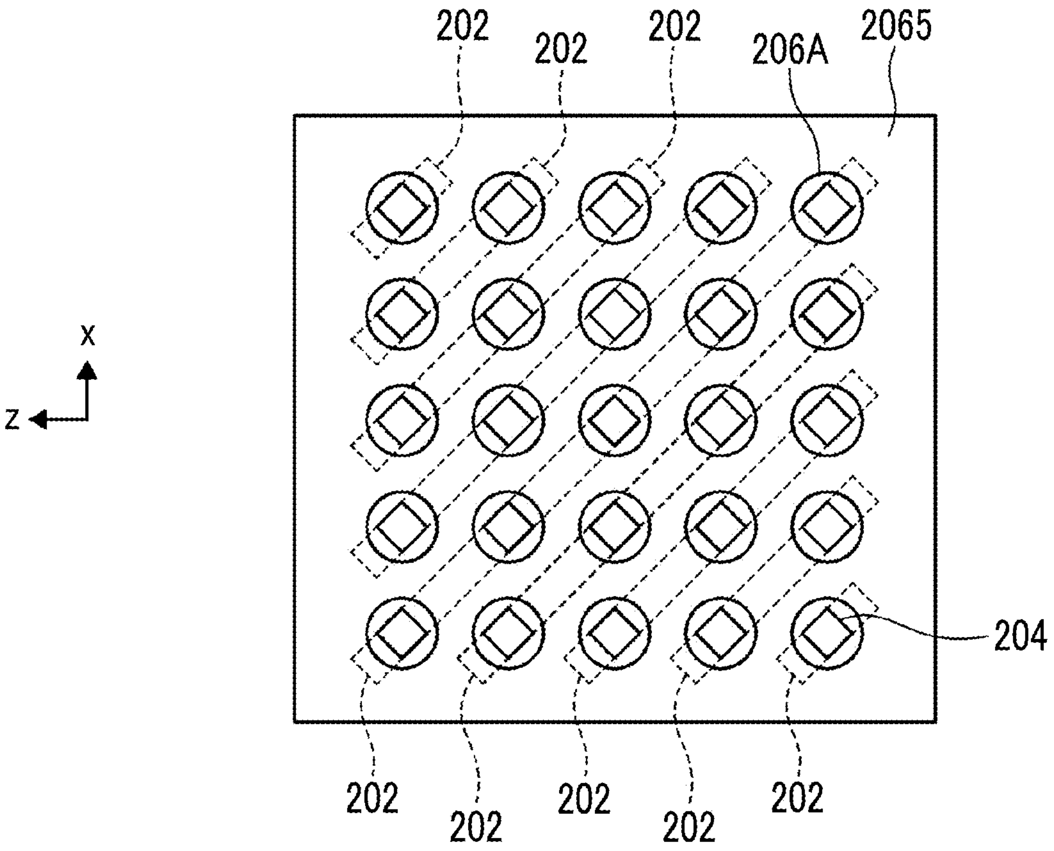
FIG. 22 is a schematic view showing a third use example of the FBG optical fiber in a case where the weight prevention cover according to the fifth structural example is applied.

FIG. 22 is a schematic view showing a third use example of the FBG optical fiber in a case where the weight prevention cover according to the fifth structural example is applied. FIG. 22 shows an aspect in which nine FBG optical fibers 202 extending in an oblique direction intersecting each of the x direction and the z direction are installed along a direction orthogonal to the direction in which the FBG optical fibers 202 extend.

Sensor Unit According to Fourth Embodiment

Figure 23:
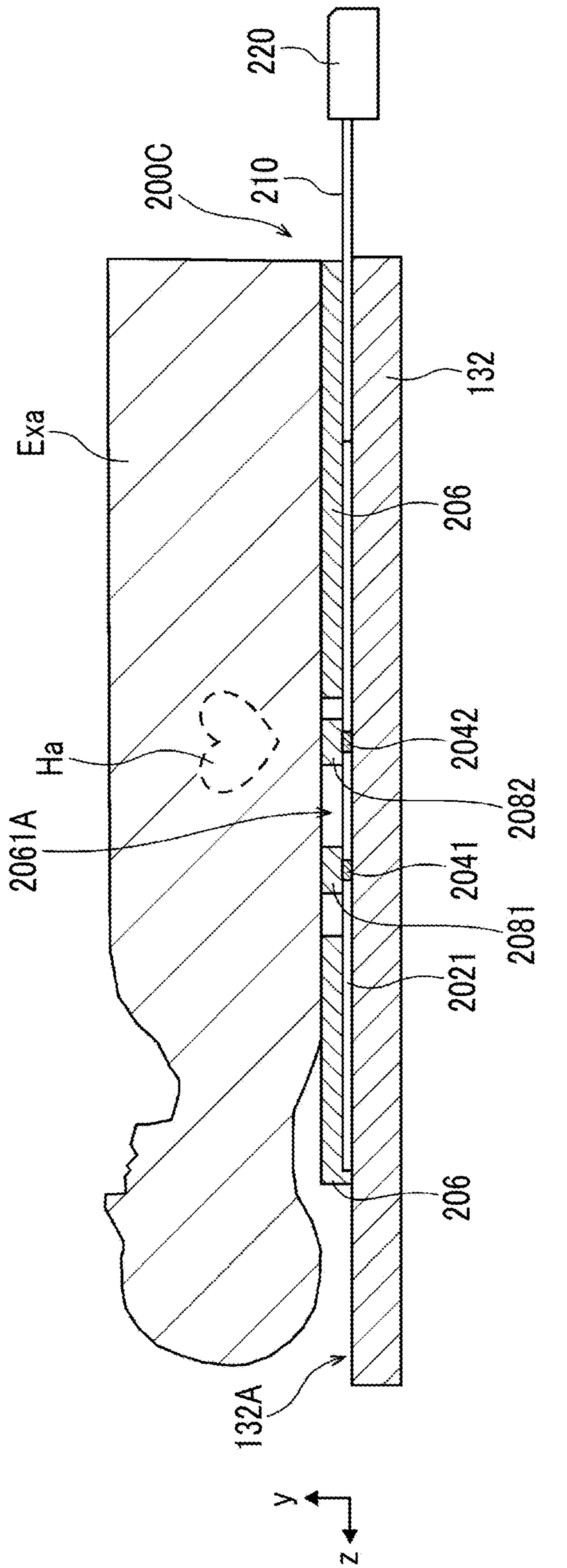
FIG. 23 is a schematic view showing a use state of a sensor unit according to a fourth embodiment.

FIG. 23 is a schematic view showing a use state of the sensor unit according to the fourth embodiment. A sensor unit 200C shown in FIG. 23 comprises an FBG optical fiber 2021 that includes a first diffraction grating 2041 and a second diffraction grating 2042. A first heartbeat propagation tool 2081 is attached to the first diffraction grating 2041. A second heartbeat propagation tool 2082 is attached to the second diffraction grating 2042. In the FBG optical fiber 2021, the optical fiber 210 is connected to a side of the second diffraction grating 2042.

In the weight prevention cover 206, a cover hole 2061A corresponding to the position and the size of a first heartbeat propagation tool 2081 and a second heartbeat propagation tool 2082 is formed. The cover hole 2061A may include a plurality of individual cover holes such as the first cover hole corresponding to the first heartbeat propagation tool 2081 and a second cover hole corresponding to the second heartbeat propagation tool 2082. The first heartbeat propagation tool 2081 is an example of a first contact assisting member according to the present disclosure, and the second heartbeat propagation tool 2082 is an example of a second contact assisting member.

The second heartbeat propagation tool 2082 close to the heart Ha of the subject Exa propagates the heartbeat of the subject Exa to the second diffraction grating 2042 with high-sensitivity. The first heartbeat propagation tool 2081 away from the heart Ha of the subject Exa is less affected by the heartbeat of the subject Exa compared to the second heartbeat propagation tool 2082, and propagates the breathing of the subject Exa to the first diffraction grating 2041 with high-sensitivity.

In addition, the FBG optical fiber 2021 does not propagate the movement of the subject Exa caused by breathing, which is 10 times or more larger than the movement of the subject Exa caused by the heartbeat, to the second diffraction grating 2042 and the reflected light propagation path of the second diffraction grating 2042 of the optical fiber 210.

On the other hand, in a case where the position of the first diffraction grating 2041 is on the side of the optical fiber 210 of the second diffraction grating 2042, the influence of the heartbeat on the first diffraction grating 2041 is small, and the movement of the subject Exa caused by the breathing is propagated with high-sensitivity to the first diffraction grating 2041, but the propagation of the reflected light of the second diffraction grating 2042 is affected.

A distance between the first heartbeat propagation tool 2081 and the second heartbeat propagation tool 2082 can be determined based on the viewpoint of propagation of the movement of the subject Exa caused by the heartbeat and propagation of the movement of the subject Exa caused by the breathing. For example, in a case where the distance between the first heartbeat propagation tool 2081 and the second heartbeat propagation tool 2082 is set to 8.0 centimeters, the above-described effects can be obtained.

The first diffraction grating 2041 is an example of a first sensor element according to the present disclosure, and the second diffraction grating 2042 is an example of a second sensor element.

Figure 24:
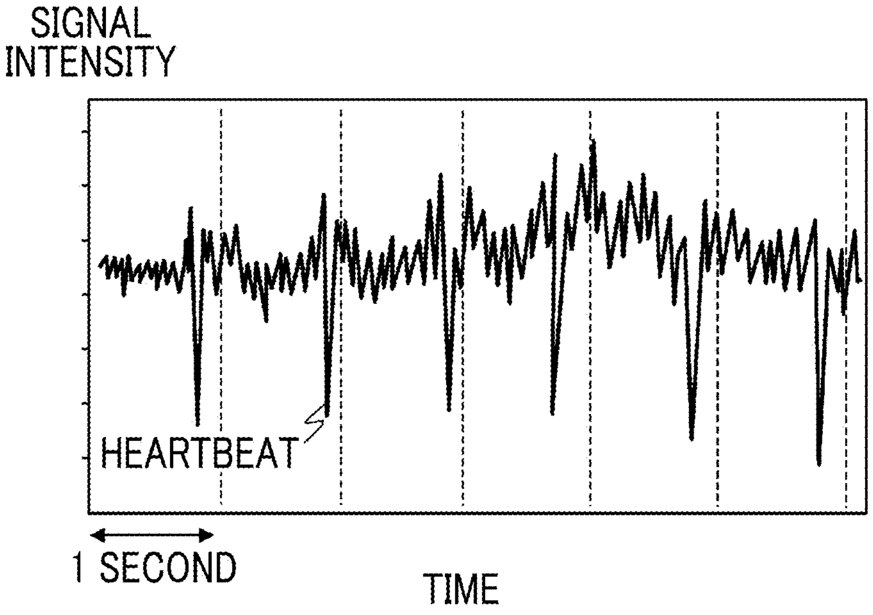
FIG. 24 is a graph showing a measurement waveform acquired using the sensor unit according to the fourth embodiment.

FIG. 24 is a graph showing a measurement waveform acquired using the sensor unit according to the fourth embodiment. In the graph shown in FIG. 24, a horizontal axis is time, and a vertical axis is signal intensity. The signal intensity is normalized.

The waveform shown in FIG. 24 is derived as a difference between a measurement waveform in which the heartbeat and the breathing are superimposed, which is obtained as the output of the second diffraction grating 2042, and the waveform of the breathing, which is obtained as the output of the first diffraction grating 2041.

In the sensor unit 200C, a heartbeat waveform in which the influence of breathing is minimized is extracted with high accuracy from the measurement waveform in which the heartbeat and the breathing are superimposed, which is obtained as the output of the second diffraction grating 2042, without using the frequency filter.

Sensor Unit According to Fifth Embodiment

Figure 25:
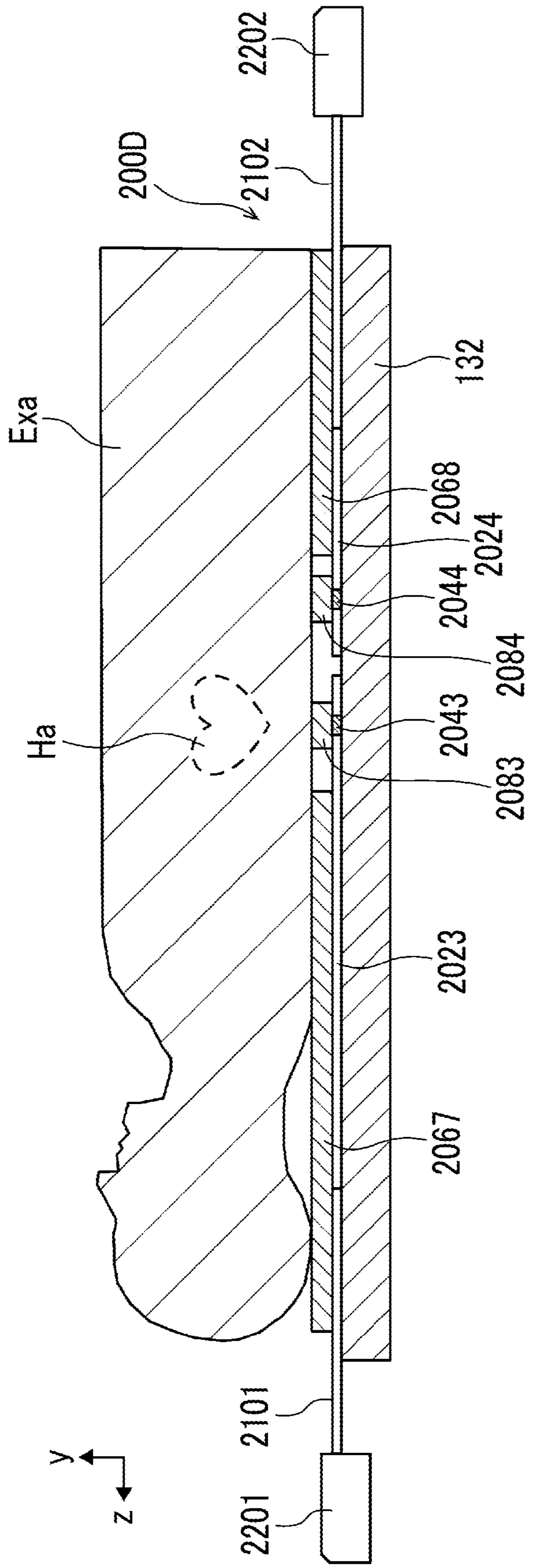
FIG. 25 is a schematic view showing a use state of a sensor unit according to a fifth embodiment.

FIG. 25 is a schematic view showing a use state of a sensor unit according to the fifth embodiment. A sensor unit 200D according to the fifth embodiment comprises a first FBG optical fiber 2023 and a second FBG optical fiber 2024 as the FBG optical fibers 202 of a plurality of systems. The first FBG optical fiber 2023 is formed with a first diffraction grating 2043, and the second FBG optical fiber 2024 is formed with a second diffraction grating 2044.

The sensor unit 200D comprises a first heartbeat propagation tool 2083 and a second heartbeat propagation tool 2084. The first heartbeat propagation tool 2083 is installed at a position directly below the heart Ha of the subject Exa in the z direction and at a position of the first diffraction grating 2043. The second heartbeat propagation tool 2084 is installed at a position closer to a lower limb side than the first heartbeat propagation tool 2083 in the z direction and at the position of the second diffraction grating 2044. For example, in the z direction, the second heartbeat propagation tool 2084 is installed at a position away from the first heartbeat propagation tool 2083 by 8 centimeters.

The sensor unit 200D comprises a first weight prevention cover 2067 and a second weight prevention cover 2068. The first weight prevention cover 2067 is installed at a position covering the first FBG optical fiber 2023. The second weight prevention cover 2068 is installed at a position covering the second FBG optical fiber 2024.

The first FBG optical fiber 2023 is connected to a first interrogator 2201 via the first optical fiber 2101. The first interrogator 2201 outputs the incidence light to the first FBG optical fiber 2023, and acquires the reflected light of the first diffraction grating 2043.

The second FBG optical fiber 2024 is connected to a second interrogator 2202 via the second optical fiber 2102. The second interrogator 2202 outputs the incidence light to the second FBG optical fiber 2024, and acquires the reflected light of the second diffraction grating 2044.

In the sensor unit 200D, a measurement waveform in which the heartbeat and the breathing are superimposed is acquired from the first interrogator 2201, and a measurement waveform of the breathing is acquired from the second interrogator 2202. The MRI apparatus 100 derives a difference between the measurement waveform in which the heartbeat and the breathing are superimposed and the measurement waveform of the breathing, as the measurement waveform of the heartbeat.

In the sensor unit 200D, a heartbeat waveform in which the influence of breathing is minimized is extracted with high accuracy from the measurement waveform in which the heartbeat and the breathing are superimposed, which is obtained as the output of the first diffraction grating 2043, without using the frequency filter.

In the present embodiment, although the sensor unit 200D comprising two systems of the FBG optical fibers 202 is exemplified, the sensor unit 200D may comprise three or more systems of the FBG optical fibers 202. As a result, a target heartbeat is extracted with high accuracy from the measurement waveform on which the plurality of components are superimposed.

The first FBG optical fiber 2023 is an example of a first fiber Bragg grating sensor according to the present disclosure, and the second FBG optical fiber 2024 is an example of a second fiber Bragg grating sensor. The first diffraction grating 2043 is an example of a first sensor element according to the present disclosure, and the second diffraction grating 2044 is an example of a second sensor element according to the present disclosure.

Sensor Unit According to Sixth Embodiment

Figure 26:
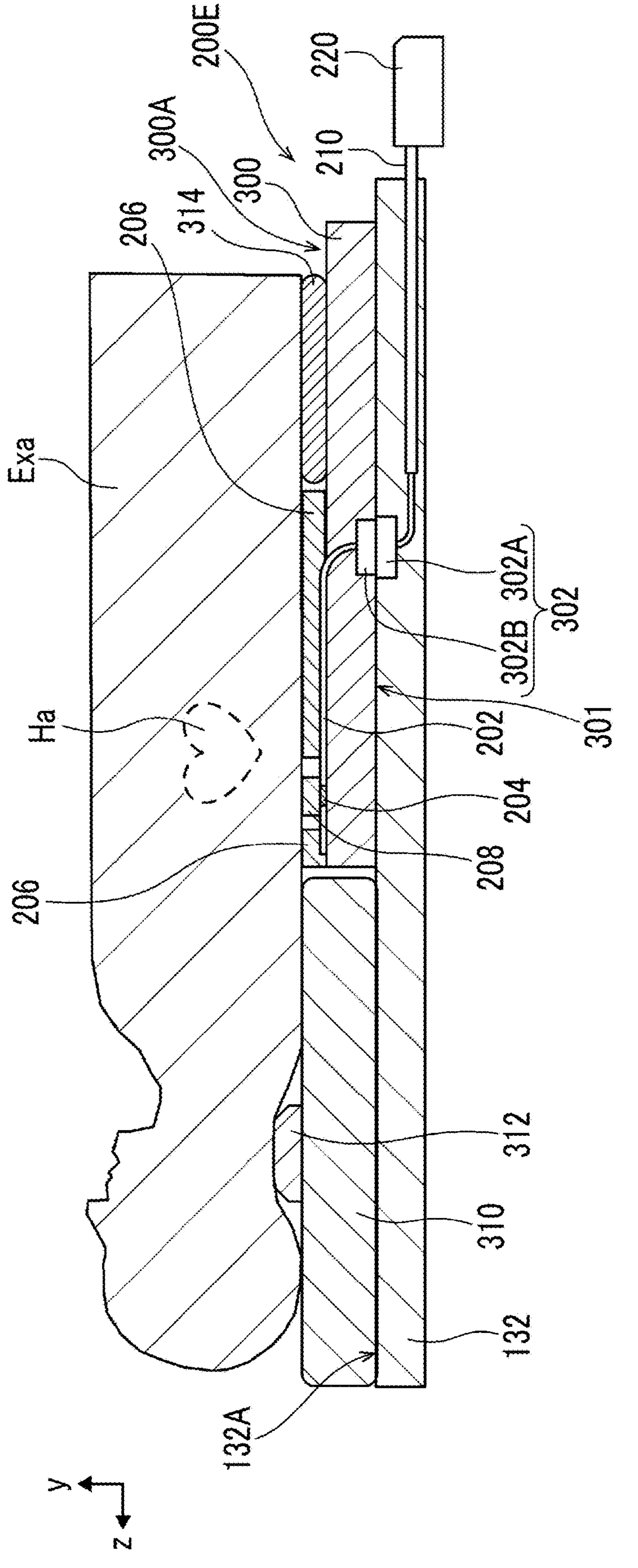
FIG. 26 is a schematic view showing a use state of a sensor unit according to a sixth embodiment.

FIG. 26 is a schematic view showing a use state of a sensor unit according to the sixth embodiment. A sensor unit 200E shown in FIG. 26 is installed on the upper surface 132A of the table 132, and the FBG optical fiber 202 is fixed to an upper surface 300A of a spine coil unit 300. As a result, the movement of the FBG optical fiber 202 in the three-dimensional space is suppressed.

The spine coil unit 300 is provided with a plurality of RF coils housed in a housing 301, electrical wirings corresponding to each of the plurality of RF coils, and the like. The upper surface 300A of the spine coil unit 300 is a surface of the housing 301 of the spine coil unit 300 on an opposite side of the table 132.

In the sensor unit 200E, similar to the sensor unit 200 and the like shown in FIG. 7, the heartbeat propagation tool 208 is installed at a position directly below the heart Ha on the back side of the subject Exa. As a result, the heartbeat of the subject Exa is propagated to the diffraction grating 204 with high-sensitivity via the heartbeat propagation tool 208.

In addition, in the sensor unit 200E, the FBG optical fiber 202 is covered with the weight prevention cover 206 on the upper surface 300A of the spine coil unit 300. As a result, the drift of the measurement waveform caused by unpredictable movements of the subject Exa is suppressed.

The sensor unit 200E comprises a connector 302 that attaches and detaches the FBG optical fiber 202, which is installed on the upper surface 300A of the spine coil unit 300, and the optical fiber 210, which is installed inside the spine coil unit 300. In the connector 302, a push-pull method is applied to attachment and detachment of a receptacle 302A and a plug 302B.

The electrical wiring of the attachable and detachable spine coil unit 300 shown in FIG. 26 may be connected to the electrical wiring inside the table 132 using a push-pull type connector installed in the vicinity of the center of the table 132. The connector 302 of the optical fiber may be added to the connector of the electrical wiring.

As a result, in a case where the spine coil unit 300 is attached to and detached from the table 132, the sensor unit 200E can be attached to and detached from the table 132.

The sensor unit 200E comprises a first mat 310, a neck rest 312, and a second mat 314. The same material as the mat 212 shown in FIG. 10 may be applied to the first mat 310 and the second mat 314. In addition, the same material and shape as those of the neck rest 216 shown in FIG. 10 may be applied to the neck rest 312.

The first mat 310 shown in FIG. 26 is placed on the upper surface 132A of the table 132 and is installed in a non-installation region where the spine coil unit 300 is not installed. FIG. 26 shows the first mat 310 that is a non-installation region of the spine coil unit 300 and is installed on a side of the head of the subject Exa.

A thickness of the first mat 310 may be the same as a thickness obtained by adding a thickness of the spine coil unit 300 and the thickness of the weight prevention cover 206. As a result, the subject Exa can relieve the hard feeling on the back, and an effect of allowing the subject Exa to relax during the measurement can be obtained.

The thickness of the first mat 310 may be thinner or thicker than the thickness obtained by adding the thickness of the spine coil unit 300 and the thickness of the weight prevention cover 206 within a range in which the above-described effects are obtained.

The neck rest 312 is installed at a position of a neck of the subject Exa and supports the neck of the subject Exa. As a result, an effect of allowing the subject Exa to relax during the measurement can be obtained.

The second mat 314 is placed on the upper surface 300A of the spine coil unit 300 and is installed in a non-installation region in which the FBG optical fiber 202 and the weight prevention cover 206 are not installed. A thickness of the second mat 314 may be the same as the thickness of the weight prevention cover 206, may be thinner than the thickness of the weight prevention cover 206, or may be thicker than the thickness of the weight prevention cover 206. As a result, the subject Exa can relieve the hard feeling on the back, and an effect of allowing the subject Exa to relax during the measurement can be obtained.

Sensor Unit According to Seventh Embodiment

Figure 27:
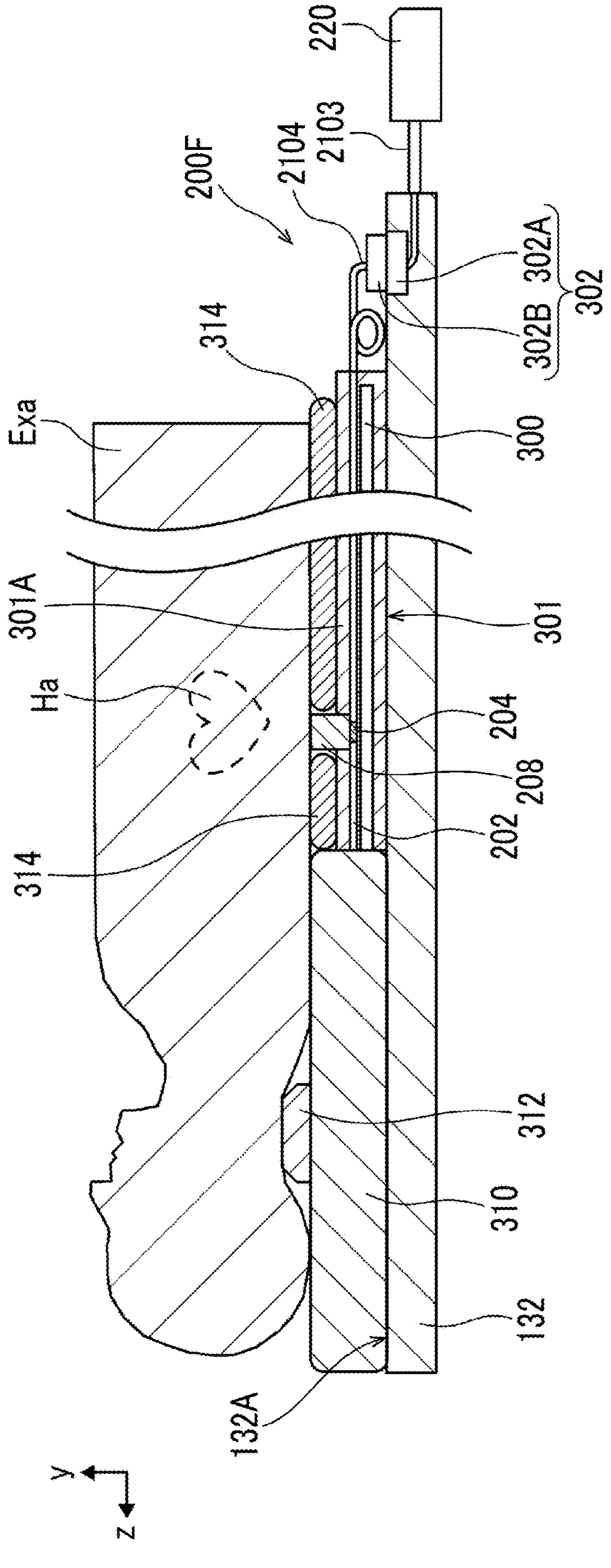
FIG. 27 is a schematic view showing a use state of a sensor unit according to a seventh embodiment.

FIG. 27 is a schematic view showing a use state of a sensor unit according to the seventh embodiment. In a sensor unit 200F shown in FIG. 27, the FBG optical fiber 202 is installed inside the housing 301 of the spine coil unit 300. Specifically, the FBG optical fiber 202 is embedded in an upper surface plate 301A of the spine coil unit 300, and a part of the upper surface plate 301A of the spine coil unit 300 functions as the fixing member that fixes the FBG optical fiber 202.

An opening is formed in the upper surface plate 301A of the housing 301 of the spine coil unit 300 at the position of the diffraction grating 204, and the diffraction grating 204 is exposed. The heartbeat propagation tool 208 is installed at a position of an opening corresponding to the diffraction grating 204.

The sensor unit 200F comprises a second optical fiber 2104, and the second optical fiber 2104 is installed outside the housing 301 of the spine coil unit 300 and is connected to the FBG optical fiber 202. The housing 301 of the spine coil unit 300 may be provided with a connector that connects the FBG optical fiber 202 and the second optical fiber 2104.

A first optical fiber 2103 is connected to the second optical fiber 2104 via the connector 302. The interrogator 220 is connected to the first optical fiber 2103. The interrogator 220 causes incidence light to be incident on the FBG optical fiber 202 via the first optical fiber 2103 and the second optical fiber 2104, and acquires the reflected light of the diffraction grating 204.

In the sensor unit 200E shown in FIG. 26, a position of the connector 302 with respect to the table 132 is fixed, and a position of the spine coil unit 300 with respect to the table 132 is fixed. In this case, in the z direction, a position of the diffraction grating 204 with respect to the table 132 is fixed, and it is difficult to adjust the position of the diffraction grating 204 in the z direction according to the position of the heart Ha of the subject Exa.

On the other hand, in the sensor unit 200F shown in FIG. 27, it is possible to adjust the position of the diffraction grating 204 in the z direction according to the position of the heart Ha of the subject Exa within a range of a length of the second optical fiber 2104.

The upper surface plate 301A of the housing 301 of the spine coil unit 300 is an example of a plate-shaped member on a side opposite to the table in the housing in which the coil provided in the coil unit according to the present disclosure is housed.

The present disclosure is not limited to the above-mentioned embodiment, and various modifications are possible within the scope of the technical concept of the present disclosure without departing from its gist.

EXPLANATION OF REFERENCES

100: MRI apparatus
110: gantry
130: bed
130A: top plate
132: table
200: sensor unit
202: FBG optical fiber
204: diffraction grating
206: weight prevention cover
206A: cover hole
208: heartbeat propagation tool

What is claimed is:

1. A sensor unit that is attached to a surface on which a subject is placed in a bed on which the subject is placed and that detects a heartbeat of the subject, the sensor unit comprising:
- a fiber Bragg grating sensor that is provided with one or more sensor elements for detecting the heartbeat of the subject;
- a fixer configured to fix a side of the fiber Bragg grating sensor opposite to a side facing the subject, the fixer having a surface on which the fiber Bragg grating sensor is fixed, the surface having a predetermined stiffness;
- a cover that covers the side of the fiber Bragg grating sensor facing the subject and that has a structure in which a cover hole is formed at a position corresponding to the sensor element on a surface of the side facing the subject; and
- a contact assisting member that has a first surface to be brought into contact with the subject through the cover hole and a second surface to be brought into contact with the sensor element in the fiber Bragg grating sensor.

2. The sensor unit according to claim 1,
wherein, in the contact assisting member, a length of the first surface to be brought into contact with the subject is longer than a length of the second surface to be brought into contact with the sensor element, in a longitudinal direction of the bed on which the sensor unit is installed.

3. The sensor unit according to claim 1, further comprising:
an elastic member that is installed at a position corresponding to the sensor element in the fiber Bragg grating sensor and located on a side of the fixer, and that has predetermined elasticity.

4. The sensor unit according to claim 1,
wherein the fixer is installed on the bed and also serves as a table on which the subject is placed.

5. The sensor unit according to claim 1,
wherein the fixer has a shape that follows a shape of a surface of a table installed on the bed, on which the sensor unit is installed.

6. The sensor unit according to claim 1,
wherein the cover has a shape that covers an entire length of the fiber Bragg grating sensor in a direction in which the fiber Bragg grating sensor extends.

7. The sensor unit according to claim 6,
wherein the cover has a shape in which the direction in which the fiber Bragg grating sensor extends is a longitudinal direction.

8. The sensor unit according to claim 6,
wherein the cover has a polygonal or circular planar shape on a surface on which the fiber Bragg grating sensor extends.

9. The sensor unit according to claim 1,
wherein the fiber Bragg grating sensor includes a first sensor element and a second sensor element that is different from the first sensor element, and
the cover has a first cover hole formed at a position corresponding to the first sensor element and a second cover hole formed at a position corresponding to the second sensor element.

10. The sensor unit according to claim 9, further comprising:
a first contact assisting member that has a first surface to be brought into contact with the subject through the first cover hole and a second surface to be brought into contact with the first sensor element in the fiber Bragg grating sensor; and
a second contact assisting member that has a first surface to be brought into contact with the subject through the second cover hole and a second surface to be brought into contact with the second sensor element in the fiber Bragg grating sensor.

11. The sensor unit according to claim 10, further comprising:
a first fiber Bragg grating sensor including the first sensor element; and
a second fiber Bragg grating sensor including the second sensor element.

12. A sensor unit that is attached to a surface on which a subject is placed in a bed on which the subject is placed and that detects a heartbeat of the subject, the sensor unit comprising:
a fiber Bragg grating sensor that is provided with one or more sensor elements for detecting the heartbeat of the subject;
a fixer configured to fix a side of the fiber Bragg grating sensor opposite to a side facing the subject, the fixer having a surface on which the fiber Bragg grating sensor is fixed, the surface having a predetermined stiffness;
a cover that covers the side of the fiber Bragg grating sensor facing the subject and that has a structure in which a cover hole is formed at a position corresponding to the sensor element on a surface of the side facing the subject; and
an elastic member that is installed on the fixer, has predetermined elasticity, and has a thickness that comes into contact with the subject.

13. A medical image capturing apparatus comprising:
a bed on which a subject is placed;
a measurement device that measures the subject;
a measurement data processing device that generates a medical image of the subject based on a measurement result of the subject; and
a sensor unit that is attached to a surface on which the subject is placed in the bed and that detects a heartbeat of the subject,
wherein the sensor unit includes
a fiber Bragg grating sensor that includes one or more sensor elements that detect the heartbeat of the subject,
a fixer configured to fix a side of the fiber Bragg grating sensor opposite to a side facing the subject, the fixer having a surface on which the fiber Bragg grating sensor is fixed, the surface having a predetermined stiffness,
a cover that covers the side of the fiber Bragg grating sensor facing the subject and that has a structure in which a cover hole is formed at a position corresponding to the sensor element on a surface of the side facing the subject, and
a contact assisting member that has a first surface to be brought into contact with the subject through the cover hole and a second surface to be brought into contact with the sensor element in the fiber Bragg grating sensor.

14. The medical image capturing apparatus according to claim 13, further comprising:
one or more processors,
wherein the one or more processors select one sensor element from among a plurality of sensor elements based on a captured image in which the subject is imaged.

15. The medical image capturing apparatus according to claim 13,
wherein the fixer is installed on the bed and also serves as a coil unit installed on a table on which the subject is placed.

16. The medical image capturing apparatus according to claim 13,
wherein, in the contact assisting member, a length of the first surface to be brought into contact with the subject is longer than a length of the second surface to be brought into contact with the sensor element, in a longitudinal direction of the bed on which the sensor unit is installed.

17. A medical image capturing apparatus comprising:
a bed on which a subject is placed;
a measurement device that measures the subject;
a measurement data processing device that generates a medical image of the subject based on a measurement result of the subject; and
a sensor unit that is attached to a surface on which the subject is placed in the bed and that detects a heartbeat of the subject,
wherein the sensor unit includes
a fiber Bragg grating sensor that includes one or more sensor elements that detect the heartbeat of the subject,
a fixer configured to fix a side of the fiber Bragg grating sensor opposite to a side facing the subject, the fixer having a surface on which the fiber Bragg grating sensor is fixed, the surface having a predetermined stiffness, and
a cover that covers the side of the fiber Bragg grating sensor facing the subject and that has a structure in which a cover hole is formed at a position corresponding to the sensor element on a surface of the side facing the subject,
wherein the fixer is installed on the bed and also serves as a coil unit installed on a table on which the subject is placed,
wherein the fiber Bragg grating sensor is embedded in a plate-shaped member on a side opposite to the table in a housing in which a coil provided in the coil unit is housed.

18. A medical image capturing apparatus comprising:
a bed on which a subject is placed;
a measurement device that measures the subject;

a measurement data processing device that generates a medical image of the subject based on a measurement result of the subject; and a sensor unit that is attached to a surface on which the subject is placed in the bed and that detects a heartbeat of the subject, wherein the sensor unit includes a fiber Bragg grating sensor that includes one or more sensor elements that detect the heartbeat of the subject, a fixer configured to fix a side of the fiber Bragg grating sensor opposite to a side facing the subject, the fixer having a surface on which the fiber Bragg grating sensor is fixed, the surface having a predetermined stiffness, a cover that covers the side of the fiber Bragg grating sensor facing the subject and that has a structure in which a cover hole is formed at a position corresponding to the sensor element on a surface of the side facing the subject, and an elastic member that is installed on the fixer, has predetermined elasticity, and has a thickness that comes into contact with the subject.

* * * * *